United States Patent
Bickers et al.

(10) Patent No.: US 9,949,485 B2
(45) Date of Patent: Apr. 24, 2018

(54) USE OF ACYLSULFONAMIDES FOR IMPROVING PLANT YIELD

(71) Applicant: BAYER CROPSCIENCE AG, Monheim (DE)

(72) Inventors: Udo Bickers, Kelkheim (DE); Stefan Lehr, Lyons (FR); Klaus Trabold, Heidelberg (DE); Mathias Schmidt, Waldems (DE); Martin Jeffrey Hills, Idstein (DE); Juan Pedro Ruiz-Santaella Moreno, Leverkusen (DE); Erwin Hacker, Langenenslingen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 104 days.

(21) Appl. No.: 14/767,025

(22) PCT Filed: Feb. 28, 2014

(86) PCT No.: PCT/EP2014/053996
§ 371 (c)(1),
(2) Date: Aug. 11, 2015

(87) PCT Pub. No.: WO2014/135468
PCT Pub. Date: Sep. 12, 2014

(65) Prior Publication Data
US 2016/0000084 A1    Jan. 7, 2016

(30) Foreign Application Priority Data
Mar. 5, 2013  (EP) ..................... 13157805

(51) Int. Cl.
| | | |
|---|---|---|
| A01N 25/32 | (2006.01) |
| A01N 25/00 | (2006.01) |
| A01N 43/36 | (2006.01) |
| A01N 43/08 | (2006.01) |
| A01N 37/02 | (2006.01) |
| A01N 47/30 | (2006.01) |
| A01N 43/653 | (2006.01) |
| C07C 317/42 | (2006.01) |

(52) U.S. Cl.
CPC ............ *A01N 47/30* (2013.01); *A01N 43/653* (2013.01); *C07C 317/42* (2013.01)

(58) Field of Classification Search
None
See application file for complete search history.

(56) References Cited

U.S. PATENT DOCUMENTS

| | | | |
|---|---|---|---|
| 7,683,086 B2 * | 3/2010 | Ammermann | A01N 43/653 514/312 |
| 8,901,040 B2 | 12/2014 | Schulz et al. | |
| 2007/0124839 A1 | 5/2007 | Schulz et al. | |
| 2010/0009852 A1 | 1/2010 | Rosinger et al. | |
| 2011/0269626 A1 | 11/2011 | James et al. | |
| 2012/0137941 A1* | 6/2012 | Vantieghem | A01C 21/00 111/100 |
| 2014/0349849 A1 | 11/2014 | Schulz et al. | |

FOREIGN PATENT DOCUMENTS

| | | | |
|---|---|---|---|
| DE | 291685 | * | 7/1991 |
| DE | 291685 A5 | | 7/1991 |
| EP | 365484 A1 | | 4/1990 |
| EP | 597807 | * | 5/1994 |
| WO | WO 9966795 | * | 12/1991 |
| WO | 9745016 A1 | | 12/1997 |
| WO | 9916744 A1 | | 4/1999 |
| WO | 20051117 A1 | | 1/2005 |
| WO | 2007062737 A2 | | 6/2007 |
| WO | 2009056333 A2 | | 5/2009 |
| WO | 2010003444 A2 | | 1/2010 |
| WO | 2012017374 A1 | | 2/2012 |
| WO | WO2012021250 | * | 2/2012 |
| WO | 2012059328 A2 | | 5/2012 |

OTHER PUBLICATIONS

International Search Report from corresponding PCT/EP2014/053996, dated May 16, 2014.
Amon et al., "Mechanisms That Help the Yeast Cell Cycle Clock Tick: G2 Cyclins Transcriptionally Activate G2 Cyclines and Repress G1 Cyclins", Cell, vol. 74, pp. 993-1007, Sep. 24, 1993.
Buchanan et al., Biochemistry & Molecular, Biology of the Plant, (2000); eds., pp. 558-563.
Buchanan et al., Biochemistry & MolecularBiology of the Plant, (2000); eds., pp. 850-929.
Buchanan et al., Biochemistry & Molecular Biology of the Plant, (2000); eds. pp. 980-985.

(Continued)

*Primary Examiner* — Alton N Pryor
(74) *Attorney, Agent, or Firm* — McBee Moore Woodward & Vanik IP, LLC

(57) ABSTRACT

Compounds (A) can be used for increasing the yield of useful plants or crop plants with respect to their harvested plant organs, wherein the Compound (A) is selected from compounds of the formula (I) or salts thereof,

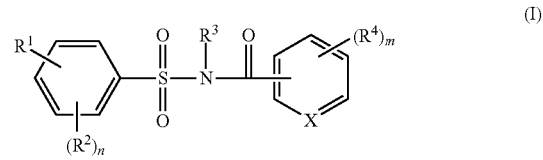

wherein the symbols are defined as in claim 1, preferably N-(2-methoxybenzoyl)-4-[(methylaminocarbonyl)-amino]benzenesulfonamide [Compound (A1)].

17 Claims, No Drawings

(56) References Cited

OTHER PUBLICATIONS

Dynlacht, "Regulation of transcription by proteins that control the cell cycle", Nature, vol. 389, Sep. 11, 1997, Macmillan Publishers Ltd, pp. 149-152.
Hunt et al., "Cell multiplication", Cell Biology, 1997, vol. 9, pp. 765-767.
Morgan, "Cyclin-Dependent Kinases: Engines, Clocks, and Microprocessors", Annu. Rev. Cell Dev. Biol. 1997, vol. 13, pp. 261-291.
Thomas et al., "TOR signalling and control of cell growth", Cell Biology, Department of Biochemistry, Basil, Switzerland, 1997, vol. 9, pp. 782-787.
Buchanan et al., Biochemistry & Molecular Biology of the Plant (2000); eds. pp. 542-565.

\* cited by examiner

USE OF ACYLSULFONAMIDES FOR IMPROVING PLANT YIELD

CROSS REFERENCE TO RELATED APPLICATIONS

This application is a § 371 National Stage Application of PCT/EP2014/053996, filed 28 Feb. 2014, which claims priority to EP 13157805.6, filed 5 Mar. 2013.

BACKGROUND

Field of the Invention

The present invention relates to the use of certain compounds [Compounds (A)] for the treatment of crop plants for inducing specific growth regulating responses on the plants, on seeds from which they grow or on the locus in which they grow in their normal habitat, preferably in the absence of extraordinary environmental conditions.

The term "method for plant growth regulation" or the term "growth regulation process" or the use of the words "plant growth regulation" or other terms using the word "regulate" as used in instant specification relate to a variety of plant responses that improve some characteristic of the plant. "Plant growth regulators" are compounds which possess activity in one or more growth regulation process(es) of a plant. Plant growth regulation is distinguished here from pesticidal action or growth reduction, sometimes also defined as a plant growth regulation, the intention of which, however, is to destroy or stunt the growth of a plant. For this reason, the compounds used in the practice of this invention are used in amounts which are non-phytotoxic with respect to the plant being treated but which stimulate the growth of the plant or certain parts thereof. Therefore, such compounds may also be called "plant stimulants", their action may be named "plant growth stimulation".

Plant growth regulation is a desirable way to improve plants and their cropping so as to obtain improved plant growth and better conditions in agriculture practice compared to non-treated plants. These kinds of molecules can either inhibit or promote cellular activities. This means that plant growth regulators identified in plants most often regulate division, elongation and differentiation of plant cells in a way that, most often, they have multiple effects in plants. The trigger event can be seen to be different in plants in comparison to the one known from animals.

On the molecular level, plant growth regulators may work by affecting membrane properties, controlling gene expression or affecting enzyme activity or being active in a combination of at least two of the before mentioned types of interaction.

Plant growth regulators are chemicals either of natural origin, also called plant hormones (like non-peptide hormones e.g. auxins, giberrellins, cytokinins, ethylene, brassinosteroids or abscisic acid, and salicilic acid), lipooligosaccharides (e.g. Nod factors), peptides (e.g. systemin), fatty acid derivatives (e.g. jasmonates), and oligosaccharins (for review see: Biochemistry & Molecular Biology of the Plant (2000); eds. Buchanan, Gruissem, Jones, pp. 558-562; and 850-929), or they can be synthetically produced compounds (like derivatives of naturally occurring plant growth hormones, ethephon). Plant growth regulators which work at very small concentrations can be found in many cells and tissues, but they seem to be concentrated in meristems and buds.

Description of Related Art

The mode of action of existing plant growth regulators is often not known. Various targets are discussed and among those, most of the affected molecules are involved in cell division regulation, like arresting the cell cycle in stage G1 or G2, respectively, others for signaling drought stress responses (Biochemistry & Molecular Biology of the Plant (2000); eds. Buchanan, Gruissem, Jones, pp. 558-560). In any case, the hormone control can be identified as an extremely complex cascade of up and down regulations which, for example, can lead to a growth stimulation of one organ or cell typus of a plant but also can lead to a repression in other organs or cell types of the same plant.

In many cases, kinases are involved either directly or indirectly in plant hormone control and among the kinases, protein kinases are central and highly specific control molecules in respect to cell cycle control. Such kinases are discussed as targets for several plant hormones, as it is the case for auxin and abscisic acid (Biochemistry & Molecular Biology of the Plant (2000); eds. Buchanan, Gruissem, Jones, pp. 542-565 and pp. 980-985; Morgan (1997), Annu. Rev. Cell. Dev. Biol., 13, 261-291; Amon et al. (1993), Cell, 74, pp. 993-1007; Dynlacht et al. (1997), Nature, 389, pp. 149-152; Hunt and Nasmyth (1997), Curr. Opin. Cell. Biol., 9, pp. 765-767; Thomas and Hall (1997), Curr. Opin. Cell Biol., 9, pp. 782-787). The preparation and use of 2-amino-6-oxypurine derivatives as plant growth regulators is described in WO20051117.

Since, however, the ecologic and economic demands on modern crop treatment compositions are increasing constantly, for example with respect to toxicity, selectivity, application rate, formation of residues and favourable manufacture, there is a constant need to develop novel crop treatment compositions which have advantages over those known, at least in some areas. It was therefore an object of the present invention to provide further compounds to be applied on plants, on seeds from which they grow or on the locus in which they grow in their normal habitat, for growth regulating responses, preferably in the absence of abiotic stress conditions. In this regard it should be mentioned that the term "absence of abiotic stress conditons" is to be understood in the context of the present invention to mean that plants or seeds are not exposed to extraordinary environmental conditions such as extreme drought, cold and hot conditions, osmotic stress, waterlogging, elevated soil salinity, elevated exposure to minerals, ozone conditions, strong light conditions, limited availability of nitrogen nutrients or limited availability of phosphorus nutrients, particularly extraordinary environmental conditions beyond normal environmental fluctuations that may occur under normal plant growing conditions. Growing in the absence of abiotic stress conditions thus encompasses growing plants in field conditions whereby the growing conditions, including nutrient supply, temperature, water supply, and other conditions are considered average to optimal for the particular crop species. Growing in the absence of abiotic stress conditions also encompasses growing plants under greenhouse conditions which are considered average to optimal for the crop species.

Generally, a superior growth may result in an improvement of growth, for example, with respect to:
germination,
root growth
shoot development,
sprouting,
flower development, photosynthesis performance of the plants,
leaves growth, preferably growth of the area of leaves,
plants per area (improved plant density).

Alternatively, the superior growth may result in an improvement of crop yield with respect to various parameters such as:
bio mass,
quantitative fruit yield,
size of fruits,
quantitative grain yield,
qualitative yield such as increase in content of desired components, e.g. sugar content of sugar beet or protein content in cereal grains, gluten content of grains for the production of glues).

While the improvement in some of the above growth characteristics may be effected together, some may be achieved very specifically with no or even adverse effects on the other parameters.

It is thus desired to provide specific useful plant growth regulation effects on crop plants, that result in superior growth of these treated plants, certain parts of these plants or specific crop yield.

A broader group of compounds selected from the group of acylsulfonamides is described in WO-A-97/45016, WO-A-99/16744 and EP-A-365484 and references cited therein; the compounds hereinafter called "Compounds (A)". From said publications it is known that the "Compounds (A)" have safener properties. Safeners are used in crops of useful plants together with pesticides, such as herbicides, insecticides or fungicides, preferably herbicides, to reduce phytotoxic effects of the pesticides on the crop plants. A good safener shall not reduce the desired effect of a pesticide on target organisms, for example the effect against weed plants in case of a herbicide as the pesticide. One Compound (A) that might work as a safener (see for example in WO2009/056333; WO2012/017374; and US2011/0269626) is N-(2-methoxybenzoyl)-4-[(methylaminocarbonyl)amino]benzenesulfonamide [CAS RN 129531-12-0], hereafter also called "Compound (A1)."

It is further known from WO 2007/062737 that acylsulfonamide safeners have also shown effects to reduce plant damage of crop plants, specifically of maize plants, against certain abiotic stress such as extraordinary drought, heat or chillness.

According to WO 2010/003444, acylsulfonamide safeners have also shown to improve root growth of crop plants, specifically of maize plants. Additionally, effects in regulating shoot growth of crop plants, specifically of maize plants, has been described in the reference too.

In WO 2012/059328, the combination of certain neonicotinoid insecticides and metabolic herbicide safeners for the treatment of of plant propagation material, like seeds for improving growing characteristics of plants has been reported.

SUMMARY

It has now been found that, surprisingly, a Compound (A), preferably Compound (A1), can be used either solely or in combination with one or more other selected agrochemical compounds for increasing the yield of useful plants or crop plants with respect to their harvested plant organs.

Another object of the invention is a method for increasing the yield of useful plants or crop plants with respect to their harvested plant organs wherein a Compound (A), specifically Compound (A1), is applied in a effective, preferably non-phytotoxic amount to the crop plants, the seeds from which they grow, or to the locus in which they grow in their normal habitat, preferably in the absence of extraordinary environmental conditions.

DETAILED DESCRIPTION OF A PREFERRED EMBODIMENT

The term "useful plants" as used here refers to crop plants which are employed as plants for obtaining foods, animal feeds or for industrial purposes as well as horticultural plants.

In the context of the present invention, the term "increasing the yield" preferably means a specific yield enhanced by or more than 2%, more preferably by or more than 5%, more preferably by or more than 8%, more preferably by or more than 10%, of the harvested plant organs compared to the untreated control plants, it being possible for the effects to manifest themselves individually or else in any combination of effects.

In the context of the present invention, the term "with respect to their harvested plant organs" define the plant organs usually harvested depending on the specific plant to be considered and products derived therefrom under harvesting. This includes the whole biomass of several plant organs if these are harvested together and then may indicate a rather unspecific general effect on plant growth. However, preferably it defines the harvested seed in case of seed producing plants, for example the seed of cereal plants including maize plants, the seed of oil plants such as oilseed rape or canola, the seed organs of legumes, for example beans, lentils, peas and soybeans.

Preferably the harvested plant organs encompass also the harvested seed organs of fiber plants such as cotton plants, preferably the lints of cotton plants taken from the seed capsules for fiber production.

Preferably the harvested plant organs encompass also the harvested organs of beet plants, such as for example sugar beet and fodder beet.

The term "with respect to their harvested plant organs" also encompasses the improvement as to specific parameters of the harvested plant organs, such as the starch content of seed kernels, the gluten content of seed kernels, the sugar content of sugar beets, the protein content of seed kernels.

Preferably, the plant organs are harvested at a mature stage of their growth or near their stage of maturity, as this is usual for harvesting.

A more preferred object of the invention is the use of or method of using Compound (A), specifically Compound (A1), either solely (i.e. as the only agrochemical compound) or in combination with one or more selected agrochemical compound(s), for increasing the grain yield of crop plants selected from group consisting of cereals, canola, soybean and cotton crops.

The term "agrochemical compound" is to be understood as meaning any compound selected from the group consisting of herbicides, fungicides, insecticides, bactericides, nematicides, acaricides, plant-growth regulators and safener.

Another preferred object of the invention is the use of or method of using Compound (A), specifically Compound (A1), either solely (i.e. as the only agrochemical compound) or in combination with one or more selected agrochemical compound(s), for increasing the protein content of seed kernels of crop plants selected from group consisting of cereals, canola and soybean crops.

Another preferred object of the invention is the use of or method of using Compound (A), specifically Compound (A1), either solely or in combination with one or more selected agrochemical compound(s), for increasing the gluten content of seed kernels of crop plants selected from group consisting of cereals, canola and soybean crops.

Another preferred object of the invention is the use of or method of using Compound (A), specifically Compound (A1), either solely or in combination with one or more selected agrochemical compound(s), for increasing the gluten content of seed kernels of crop plants selected from group consisting of cereal crops.

Another preferred object of the invention is the use of or method of using Compound (A), specifically Compound (A1), either solely or in combination with one or more selected agrochemical compound(s), for increasing the yield of the amount by weight of beets of beet plants.

Another preferred object of the invention is the use of or method of using Compound (A), specifically Compound (A1), either solely or in combination with one or more selected agrochemical compound(s), for increasing the biomass yield of maize plants growing in the absence of extraordinary environmental conditions.

Another preferred object of the invention is the use of or method of using Compound (A), specifically Compound (A1), either solely or in combination with one or more selected agrochemical compound(s), for increasing the sugar content of sugar beets.

Another preferred object of the invention is the use of or method of using Compound (A), specifically Compound (A1), either solely or in combination with one or more selected agrochemical compound(s), for increasing the biomass yield of sugar plants.

Another preferred object of the invention is the use of or method of using Compound (A), specifically Compound (A1), either solely or in combination with one or more selected agrochemical compound(s), for increasing the biomass yield of sugar beet plants growing in the absence of extraordinary environmental conditions.

A more preferred object of the invention is the use of or method of using Compound (A), specifically Compound (Al), either solely or in combination with one or more selected agrochemical compound(s), for increasing the grain yield of cereal crops, preferably wheat, barley, rye, triticale, rice, sorghum, sugarcane or maize crops.

A more preferred object of the invention is also the use of or method of using Compound (A), specifically Compound (Al), either solely or in combination with one or more selected agrochemical compound(s), for increasing the germination and emergence of rice crops.

A more preferred object of the invention is also the use of or method of using Compound (A), specifically Compound (Al), either solely or in combination with one or more selected agrochemical compound(s), for increasing the grain yield of oil crops such as canola crops.

A more preferred object of the invention is also the use of or method of using Compound (A), specifically Compound (Al), either solely or in combination with one or more selected agrochemical compound(s), for increasing the bean yield of legume crops such as soybean crops.

A more preferred object of the invention is also the use of or method of using Compound (A), specifically Compound (A1), either solely or in combination with one or more selected agrochemical compound(s), for increasing the grain yield of fiber crops such as cotton crops.

A more preferred object of the invention is also the use of or method of using Compound (A), specifically Compound (A1), either solely or in combination with one or more selected agrochemical compound(s), for increasing the lints yield of fiber crops such as cotton crops.

A more preferred object of the invention is also the use of or method of using Compound (A), specifically Compound (A1), either solely or in combination with one or more selected agrochemical compound(s), for increasing the beet yield of beet crops such as sugar beet crops.

Another preferred object of the invention is the use of or method of using Compound (A), specifically Compound (A1), either solely or in combination with one or more selected agrochemical compound(s), for increasing the biomass yield of sugar beet or sugarcane plants.

Compounds (A) according to the present invention are understood as being selected from compounds of the formula (I) or salts thereof,

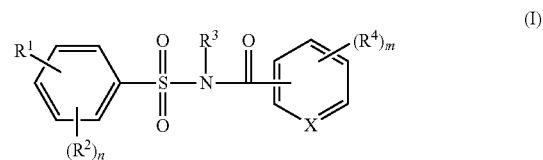

(I)

wherein
X is CH;
$R^1$ is —NH—CO—$NR^5R^6$,
$(R^2)_n$ is a radical $R^2$ if n is 1 or represents n radicals $R^2$ attached to different carbon ring atoms of the basic ring if n is more than 1, wherein each $R^2$ independently of one another is halogen, $(C_1-C_4)$haloalkyl, $(C_1-C_4)$haloalkoxy, nitro, $(C_1-C_4)$alkyl, $(C_1-C_4)$alkoxy, $(C_1-C_4)$alkylsulfonyl, $[(C_1-C_4)$alkoxy]carbonyl or $[(C_1-C_4)$alkyl]carbonyl,
$R^3$ is hydrogen, $(C_1-C_4)$alkyl, $(C_2-C_4)$alkenyl or $(C_2-C_4)$alkinyl,
$(R^4)_m$ is a radical $R^4$ if m is 1 or represents m radicals $R^4$ attached to different carbon ring atoms of the basic ring if m and is more than 1, wherein each $R^4$ independently of one another is halogen, nitro, $(C_1-C_4)$alkyl, $(C_1-C_4)$haloalkyl, $(C_1-C_4)$haloalkoxy, $(C_3-C_6)$cycloalkyl, phenyl, $(C_1-C_4)$alkoxy, cyano, $(C_1-C_4)$alkylthio, $(C_1-C_4)$alkylsulfinyl, $(C_1-C_4)$alkylsulfonyl, $[(C_1-C_4)$alkoxy]carbonyl or $[(C_1-C_4)$alkyl]carbonyl;
$R^5$ is hydrogen, $(C_1-C_8)$alkyl, $(C_2-C_6)$alkenyl, $(C_2-C_6)$alkinyl or $(C_3-C_8)$cycloalkyl, wherein each of the last-mentioned 4 radicals is unsubstituted or substituted by 1, 2 or 3 radicals selected from the group consisting of halogen, $(C_1-C_4)$alkoxy, $(C_1-C_6)$haloalkoxy and $(C_1-C_4)$alkylthio and, in case of cyclic basic radicals, also $(C_1-C_4)$alkyl and $(C_1-C_4)$haloalkyl,
$R^6$ is hydrogen, $(C_1-C_8)$alkyl, $(C_2-C_6)$alkenyl, $(C_2-C_6)$alkinyl or $(C_3-C_8)$cycloalkyl, wherein each of the last-mentioned 4 radicals is unsubstituted or substituted by 1, 2 or 3 radicals selected from the group consisting of halogen, $(C_1-C_4)$alkoxy, $(C_1-C_6)$haloalkoxy and $(C_1-C_4)$alkylthio and, in case of cyclic basic radicals, also $(C_1-C_4)$alkyl and $(C_1-C_4)$haloalkyl,
n is 0, 1, 2, 3 or 4, preferably 0, 1 or 2, and
m is 0, 1, 2, 3 or 4, preferably 1 or 2.

More preferred Compounds (A) are compounds of the formula (I) or salts thereof,
wherein
X is CH;
$R^1$ is —NH—CO—$NR^5R^6$,
$(R^2)_n$ is a radical $R^2$ if n is 1 or represents n radicals $R^2$ attached to different carbon ring atoms of the basic ring if n is more than 1, wherein each $R^2$ independently of one another is halogen, $(C_1-C_2)$haloalkyl, $(C_1-C_2)$haloalkoxy, nitro, $(C_1-C_2)$alkyl, $(C_1-C_2)$alkoxy, $(C_1-C_2)$alkylsulfonyl, $[(C_1-C_2)$alkoxy]carbonyl or $[(C_1-C_2)$alkyl]carbonyl, $R^3$ is hydrogen $(R^4)_m$ is a radical $R^4$ if m is 1 or represents m radicals $R^4$ attached to different carbon ring atoms of the basic ring if m and is more than 1, wherein each $R^4$ independently of one another is halogen, nitro, $(C_1-C_2)$alkyl, $(C_1-C_2)$haloalkyl, $(C_1-C_2)$haloalkoxy, $(C_3-C_6)$cycloalkyl, $(C_1-C_2)$alkoxy, cyano, $[(C_1-C_2)$alkoxy]carbonyl or $[(C_1-C_2)$alkyl]carbonyl;

$R^5$ is hydrogen, $(C_1-C_2)$alkyl, $R^6$ is hydrogen, $(C_1-C_2)$alkyl, n is 0, 1, or 2, preferably 0, or 1, most preferably 0 m is 0, 1, or 2, preferably 1 or 2, most preferably 1

Even more preferred, Compound (A) is N-(2-methoxybenzoyl)-4-[(methylaminocarbonyl)amino]benzenesulfonamide (=Compound (A1))

Such compounds are known from EP-A-0365484.

By addition of a suitable inorganic or organic acid, such as, for example, HCl, HBr, $H_2SO_4$ or $HNO_3$, but also oxalic acid or sulfonic acids, onto a basic group, such as, for example, amino or alkylamino, the compounds of the formula (I) may form salts. Suitable substituents present in deprotonated form, such as, for example, sulfo or carboxy groups, may form inner salts with groups which for their part can be protonated, such as amino groups. Salts may also be formed by replacing the hydrogen of suitable substituents, such as, for example, sulfo or carboxy groups, or the acidic hydrogen atom of a —$SO_2$NHCO— group by an agriculturally suitable cation. These salts are, for example, metal salts, in particular alkali metal salts or alkaline earth metal salts, especially sodium salts and potassium salts, or else ammonium salts, salts with organic amines or quaternary ammonium salts.

The compounds of the formula (I) and agriculturally acceptable salts thereof used in accordance with the invention are also referred to hereinafter as "compounds of the formula (I)" for short", or also Compounds (A).

In the description of the formulae, including the accompanying claims, the aforementioned substituents have the following meanings:

Halogen means fluorine, chlorine, bromine or iodine.

The term "halo" before the name of a radical means that this radical is partially or completely halogenated, that is to say substituted by F, Cl, Br or I in any combination. The expression "$(C_1-C_6)$alkyl" means an unbranched or branched non-cyclic saturated hydrocarbon radical having 1, 2, 3, 4, 5 or 6 carbon atoms (indicated by a range of C-atoms in the parenthesis), such as, for example a methyl, ethyl, propyl, isopropyl, 1-butyl, 2-butyl, 2-methylpropyl or tert-butyl radical. The same applies to alkyl groups in composite radicals such as "alkoxyalkyl".

Alkyl radicals and also in composite groups, unless otherwise defined, preferably have 1 to 4 carbon atoms.

"$(C_1-C_6)$Haloalkyl" means an alkyl group mentioned under the expression "$(C_1-C_6)$alkyl" in which one or more hydrogen atoms are replaced by the same number of identical or different halogen atoms, such as monohaloalkyl, perhaloalkyl, $CF_3$, $CHF_2$, $CH_2F$, $CHFCH_3$, $CF_3CH_2$, $CF_3CF_2$, $CHF_2CF_2$, $CH_2FCHCl$, $CH_2Cl$, $CCl_3$, $CHCl_2$ or $CH_2CH_2Cl$. "$[(C1-C4)$alkoxy]$(C_1-C_6)$alkyl" means $(C_1-C_6)$ alkyl which is substituted by one or more $(C_1-C_4)$alkoxy groups, preferably by one $(C_1-C_4)$alkoxy group.

"$(C_1-C_6)$Alkoxy" means an alkoxy group whose carbon chain has the meaning given under the expression "$(C_1-C_6)$alkyl". "Haloalkoxy" is, for example, $OCF_3$, $OCHF_2$, $OCH_2F$, $CF_3CF_2O$, $OCH_2CF_3$ or $OCH_2CH_2Cl$.

"$(C_2-C_6)$Alkenyl" means an unbranched or branched non-cyclic carbon chain having a number of carbon atoms which corresponds to this stated range and which contains at least one double bond which can be located in any position of the respective unsaturated radical. "$(C_2-C_6)$alkenyl" accordingly denotes, for example, the vinyl, allyl, 2-methyl-2-propenyl, 2-butenyl, pentenyl, 2-methylpentenyl or the hexenyl group.

"$(C_2-C_6)$alkynyl" means an unbranched or branched non-cyclic carbon chain having a number of carbon atoms which corresponds to this stated range and which contains one triple bond which can be located in any position of the respective unsaturated radical. "$(C_2-C_6)$alkynyl" accordingly denotes, for example, the propargyl, 1-methyl-2-propynyl, 2-butynyl or 3-butynyl group.

"$(C_3-C_6)$cycloalkyl" denotes monocyclic alkyl radicals, such as the cyclopropyl, cyclobutyl, cyclopentyl or cyclohexyl radical.

"$(C_4-C_6)$cycloalkenyl" denotes a carbocyclic, nonaromatic, partially unsaturated ring having 4 to 6 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl.

The expression "one or more radicals selected from the group consisting of" in the definition is to be understood as meaning in each case one or more identical or different radicals selected from type of radicals defined, unless specific limitations are defined expressly.

According to the type and linkage of the substituents, the compounds of the formula (I) may be present as stereoisomers. The possible stereoisomers defined by the specific three-dimensional form thereof, such as enantiomers, diastereomers, Z and E isomers, are all encompassed by the formula (I). When, for example, one or more alkenyl groups are present, diastereomers (Z and E isomers) may occur. When, for example, one or more asymmetric carbon atoms are present, enantiomers and diastereomers may occur. Stereoisomers can be obtained from the mixtures obtained in the preparation by customary separation methods. The chromatographic separation can be effected either on the analytical scale to find the enantiomeric excess or the diastereomer excess, or else on the preparative scale to produce test specimens for biological testing. It is likewise possible to selectively prepare stereoisomers by using stereoselective reactions with use of optically active starting materials and/or assistants. The invention thus also relates to all stereoisomers which are encompassed by the formula (I) but are not shown with their specific stereoisomeric form, and mixtures thereof.

The radical definitions stated above, in general terms or listed within areas of preference, apply both to the end products of the formula (I) and correspondingly to the starting materials and intermediates required for the preparation in each case. These radical definitions can be exchanged with one another, i.e. including combinations between the preferred ranges stated.

The term "useful plants" as used here refers to crop plants which are employed as plants for obtaining foods, animal feeds or for industrial purposes as well as horticultural plants.

The present invention further provides a method for treatment of plants, preferably growing in the absence extraordinary environmental conditions. With "absence of any kind of extraordinary environmental conditions" is to be understood in the context of the present invention to mean that plants or seeds are not exposed to extraordinary environmental conditions such as extreme drought, cold and hot conditions, osmotic stress, waterlogging, elevated soil salinity, elevated exposure to minerals, ozone conditions, strong light conditions, limited availability of nitrogen nutrients or limited availability of phosphorus nutrients, particularly extraordinary environmental conditions beyond normal environmental fluctuations that may occur under normal plant growing conditions.

A Compound (A), specifically Compound (A1), may be applied by seed treatment or by preemergence or postemergence applications, for example under conditions which are known in the art.

The Compound (A), specifically Compound (A1), may be applied either solely or in combination with one or more agrochemical compound(s) by seed treatment or by preemergence or postemergence applications, for example under conditions which are known in the art.

The pre-emergence or post-emergence applications may use spray techniques applying spray solutions of Compound (A), specifically Compound (A1), either solely or in combination with one or more agrochemical compound(s). Such spray solutions may comprise other customary constituents, such as solvents, formulation aids, especially water. Further constituents may include active agrochemical ingredients described below.

The present invention further provides for the use of corresponding spray solutions for increasing the yield of useful plants or crop plants with respect to their harvested plant organs. The remarks which follow apply both to the inventive use of the compounds of the formula (I) per se and to the corresponding spray solutions.

When using Compound (A), specifically Compound (A1), either solely or in combination with one or more agrochemical compound(s), as a plant growth regulator for increasing the yield of useful plants with respect to their harvested plant organs, for example for increasing the grain yield of crop plants like those mentioned above, preferably cereal plants, such as wheat, barley, rye, triticale, millet, rice or corn (maize), the application rate is, for example, in the range of from 0.005 (5 mg) to 5000 g active substance per hectare of soil surface, preferably in the range of from 0.01 (10 mg) to 2000 g/ha, in particular in the range of from 0.05 (50 mg) to 1000 g/ha of active substance, very particularly from 10 to 1000 g/ha of active substance, more preferred from 20 to 500 g/ha of active substance, mostly preferred from 25 to 100 g/ha of active substance.

A Compound (A), specifically Compound (A1), either solely or in combination with one or more agrochemical compound(s), can be applied to the plants by spraying spray solutions containing the Compound (A), specifically Compound (A1), by distributing granules containing the Compound (A), specifically Compound (A1), on the soil of the cultivated area, by pouring solutions or dispersions or granules containing Compound (A), specifically Compound (A1), into the field water (e.g. paddy-rice).

A Compound (A), specifically Compound (A1), either solely or in combination with one or more agrochemical compound(s), can be applied the pre-emergence method (pre-sown or similtaneous with sowing, e. g. pre-plant incorporated or in-furrow treatment, or after sowing) or the earyl post-emergence method or later in the post-emergence period, generally up to full bloom of the useful plants.

As an alternative, application as plant growth regulator is also possible by treating the seed, which includes various techniques for dressing and coating seed. Here, the application rate depends on the particular techniques and can be determined in preliminary tests. Generally, the application rate of Compound (A), specifically Compound (A1), as active substance in case of a seed treatment is from 0.001 (1 mg) to 10 grammes active substance (a. i.) per kilogramme seed, preferably 0.01 (10 mg) to 5 g a. i. per kg seed, in particular 0.1 (100 mg) to 2 g a. i. per kilogramme seed.

If solutions of Compounds (A), preferably Compound (A1), either solely or in combination with one or more agrochemical compound(s), are used in the seed treatment method wherein the seeds are soaked in the active substance's solution, the concentration of the active substance (a. i.) in the solution is for example from 1 to 15000 ppm, preferably 10 to 10000 ppm, more preferably 100 to 5000 ppm based on weight.

The plant growth regulator is generally applied in a plant-growth-regulating non-phytotoxic effective amount. By "non-phytotoxic" is meant an amount of the plant growth regulator which causes at most minor or no injury to the desired crop species as regards yield of harvested product.

When applying the Compound (A), specifically Compound (A1), either solely or in combination with other agrochemical compounds), it can be applied once or by split application in two or more instances while the single application can be by seed treatment, pre- or post-emergence. Therefore, it is possible to have combined applications such as by seed treatment followed by one or more pre- and/or post-emergence treatments.

Preferred application is by seed treatment.

Also preferred is single pre-emergence treatment.

Also preferred is a single post-emergence treatment.

Also preferred is a pre-emergence treatment followed by 1, 2 or 3 post-emergence treatments.

Also preferred is a seed treatment followed by 1, 2 or 3 post-emergence treatments.

Also preferred is a post-emergence treatment in the stage betweed early earing and 8 leaves stage.

Also preferred is a post-emergence treatment of the plants producing seed in the late vegetation stage up to the generative stage (between end of shooting and early bloom).

The Compounds (A), specifically (A1), can be used as stand alone product or in combination with one or more other agrochemical compounds, preferably a pesticide or plant-growth regulator more preferably a pesticide for which the plant growth regulator can effectively be used also as a safener. Of particular interest are combinations of Compounds (A), preferably Compound (A1), with herbicides, fungicides, insecticides, or plant-growth regulators especially preferred is the combination with one or more, preferably one or two agrochemically active compounds belonging to the class of fungicides.

A further preferred object of present invention is the combined use of Compound (A), specifically Compound (A1), in combination with one or more fungicides, one or more insecticides, and/or one or more plant growth regulators.

More specifically, the fungicides to be combined with Compound (A) or Compound (A1), preferably Compound (A1) are selected from the group consisiting of: benalaxyl [=F-1], benalaxyl-M [=F-2], bupirimate [=F-3], chiralaxyl [=F-4], clozylacon [=F-5], dimethirimol [=F-6], ethirimol [=F-7], furalaxyl [=F-8], hymexazole [=F-9], metalaxyl [=F-10], metalaxyl-M [=F-11], ofurace [=F-12], oxadixyl [=F-13], oxolinic acid [=F-14], benomyl [=F-15], carbendazim [=F-16], diethofencarb [=F-17], fuberidazole [=F-18], fluopicolide [=F-19], pencycuron [=F-20], thiabendazole [F-21], thiophanate-methyl [=F-22], zoxamide [F-23], chloro-7-(4-methylpiperidin-1 -yl)-6-(2,4,6-trifluorophenyl)[1,2,4]triazolo[1,5-a]pyrimidine [=F-24], diflumetorim [=F-25], bixafen [=F-26], boscalid [=F-27], carboxin [=F-28], diflumethorim [=F-29], fenfuram [=F-30], fluopyram [=F-31], flutolanil [=F-32], furametpyr [=F-33], mepronil [=F-34], oxycarboxin [=F-35], penflufen [=F-36], penthiopyrad [F-37], thifluzamid [=F-38], N-[2-(1,3-dimethylbutyl)phenyl]-5-fluoro-1,3-dimethyl-1H-pyrazole-4-carboxamide [=F-39], isopyrazam [=F-40], sedaxane HF-41], 3-(difluoromethyl)-1-methyl-N-(3',4',5'-trifluorobiphenyl-2-yl)-1H-pyrazole-4-carboxamide [=F-42], 3-(difluoromethyl)-1-methyl-N-[2-(1,1,2,2-tetrafluoroethoxy)phenyl]-1H-pyrazole-4-carboxamide [=F-43], 3-(difluoromethyl)-N-[4-fluoro-2-(1,1,2,3,3,3-hexafluoropropoxy)phenyl]-1-methyl-1H-pyrazole-4-carboxamide [F-44], N-[1-(2,4-dichlorophenyl)-1-methoxypropan-2-yl]-3-(difluoromethyl)-1-methyl-1H-pyrazole-4-carboxamide [=F-45] and corresponding salts, amisulbrom [=F-46], azoxystrobin [=F-47], cyazofamid [=F-48], dimoxystrobin [=F-49], enestrobin [=F-50], famoxadon [=F-51], fenamidone [=F-52], fluoxastrobin [=F-53], kresoxim-methyl [=F-54], metominostrobin [=F-55], orysastrobin [=F-56], pyraclostrobin [=F-57], pyribencarb [=F-58], picoxystrobin [=F-59], trifloxystrobin [=F-60], (2E)-2-(2-{[6-(3-chloro-2-methylphenoxy)-5-fluoropyrimidin-4-yl]oxy}phenyl)-2-(methoxyimino)-N-methylethanamide [=F-61], (2E)-2-(ethoxyimino)-N-methyl-2-(2-{[({(1E)-1-[3-(trifluoromethyl)-phenyl]ethylidene}amino)oxy]methyl}phenyl)ethanamide [=F-62] and corresponding salts, (2E)-2-(methoxyimino)-N-methyl-2-{2-[(E)-({1-[3-(trifluoromethyl)¬ phenyl]-ethoxy}¬ imino)methyl]phenyl}ethanamide [=F-63], (2E)-2-{2-[({[(1E)-1-(3-{[(E)-1-fluoro-2-phenylethenyl]oxy}phenyl)ethylidene]-amino}oxy)methyl]phenyl}-2-(methoxyimino)-N-methyl¬ ethanamide [=F-64], (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide [F-65], 5-methoxy-2-methyl-4-(2-{[({(1E)-1-[3-(trifluoromethyl)¬ phenyl]-ethylidene}¬ amino)¬ oxy]¬ methyl}¬ phenyl)-2,4-dihydro-3H-1,2,4-triazol-3-one [=F-66], 2-methyl {2-[({cyclopropyl[(4-methoxyphenyl)¬ imino]methyl}sulfanyl)methyl]phenyl}-3-methoxyacrylate [=F-67], N-(3-ethyl-3,5,5-trimethylcyclohexyl)-3-(formylamino)-2-hydroxybenzamide [=F-68] and corresponding salts, dinocap [=F-69], fluazinam [=F-70], fentin acetate [=F-71], fentin chloride [=F-72], fentin hydroxide [=F-73], silthiofam [=F-74], andoprim [=F-75], blasticidin-S [=F-76], cyprodinil [=F-77], kasugamycin [=F-78], kasugamycin hydrochloride hydrate [=F-79], mepanipyrim [=F-80], pyrimethanil [=F-81], fenpiclonil [=F-82], fludioxonil [=F-83], quinoxyfen [=F-84], chlozolinate [=F-85], iprodione [=F-86], procymidone [=F-87], vinclozolin [=F-88], ampropylfos [=F-89], potassium-ampropylfos [=F-90], edifenphos [=F-91], iprobenfos (IBP) [=F-92], isoprothiolane [=F-93], pyrazophos [=F-94], tolclofos-methyl [=F-95], biphenyl [=F-96], iodocarb [=F-97], propamocarb [F-98], propamocarb hydrochloride [=F-99], fenhexamid [=F-100], azaconazole [=F-101], bitertanol [=F-102], bromuconazole [=F-103], diclobutrazole [=F-104], difenoconazole [=F-105], diniconazole [=F-106], diniconazole-M [=F-107], epoxiconazole [=F-108], etaconazole [=F-109], fenbuconazole [=F-110], fluquinconazole [=F-111], flusilazole [=F-112], flutriafol [=F-113], furconazole [=F-114], furconazole-cis [=F-115], hexaconazole [=F-116], imibenconazole [=F-117], ipconazole [=F-118], metconazole [=F-119], myclobutanil [=F-120], paclobutrazole [=F-121], penconazole [=F-122], propiconazole [=F-123], prothioconazole [=F-124], simeconazole [=F-125], spiroxamine [=F-126], tebuconazole [=F-127], triadimefon [=F-128], triadimenol [=F-129], triticonazole [=F-130], uniconazole [=F-131], voriconazole [=F-132], imazalil [=F-133], imazalil sulphate [=F-134], oxpoconazole [=F-135], fenarimol [=F-136], flurprimidol [=F-137], nuarimol [=F-138], pyrifenox [=F-139], triforin [=F-140], pefurazoat [=F-141], prochloraz [=F-142], triflumizole [=F-143], viniconazole [=F-144], aldimorph [=F-145], dodemorph [=F-146], dodemorph acetate [=F-147], fenpropimorph [=F-148], tridemorph [=F-149], fenpropidin [=F-150], naftifin [=F-151], pyributicarb [=F-152], terbinafin [=F-153], 1-(4-chlorophenyl)-2-(1H-1,2,4-triazol-1-yl)cycloheptanol [=F-154], methyl 1-(2,2-dimethyl-2,3-dihydro-1H-inden-1-yl)-1H-imidazole-5-carboxylate [=F-155], N'-{5-(difluoromethyl)-2-methyl-4-[3-(trimethyl-silyl)propoxy]phenyl}-N-ethyl-N-methylimidoformamide [=F-156], N-ethyl-N-methyl-N'-{2-methyl-5-(trifluoromethyl)-4-[3-(trimethylsilyl)propoxy]phenyl}imidoformamide [=F-157], O-{1-[(4-methoxyphenoxy)methyl]-2,2-dimethylpropyl}-1H-imidazole-1-carbothioate [=F-158], benthiavalicarb [=F-159], bialaphos [=F-160], dimethomorph [=F-161], flumorph [=F-162], iprovalicarb [=F-163], polyoxins [=F-164], polyoxorim [=F-165], validamycin A [=F-166], capropamide [=F-167], diclocymet [=F-168], fenoxanil [=F-169], phthalide [=F-170], pyroquilon [=F-171], tricyclazole [=F-172], acibenzolar-S-methyl [=F-173], probenazole [=F-174], tiadinil [=F-175], isotianil [=F-176], captafol [=F-177], captan [=F-178], chlorothalonil [=F-179], copper salts such as: copper hydroxide [=F-180], copper naphthenate [F-181], copper oxychloride [=F-182], copper sulphate [=F-183], copper oxide [=F-184], oxine-copper [=F-185], Bordeaux mixture [=F-186], dichlofluanid [=F-187], dithianon [=F-188], dodine [=F-189], dodine free base [=F-190], ferbam [=F-191], folpet [=F-192], fluorofolpet [=F-193], guazatine [=F-194], guazatine acetate [=F-195], iminoctadine [=F-196], iminoctadine albesilate [=F-197], iminoctadine triacetate [=F-198], mancopper [=F-199], mancozeb [=F-200], maneb [=F-201], metiram [=F-202], metiram zinc [=F-203], propineb [=F-204], sulfur and sulfur preparations containing calcium polysulfide [=F-205], thiram [=F-206], tolylfluanid [=F-207], zineb [=F-208], ziram [=F-209], amibromdol [=F-210], benthiazole [=F-211], bethoxazin [=F-212], capsimycin [=F-213], carvone [=F-214], chinomethionat [=F-215], chloropicrin [=F-216], cufraneb [=F-217], cyflufenamid [=F-218], cymoxanil [=F-219], dazomet [=F-220], debacarb [=F-221], diclomezine [=F-222], dichlorophen [=F-223], dicloran [=F-224], difenzoquat [=F-225], difenzoquat methyl sulphate[=F-226], diphenylamine [=F-227], ethaboxam [=F-228], ferimzone [=F-229], flumetover [=F-230], flusulfamide [=F-231], fluopicolid [=F-232], fluoroimid [=F-233], fosatyl-Al [=F-234], hexachlorobenzene [=F-235], 8 hydroxy¬ quinoline sulphate [=F-236], iprodione [=F-237], irumamycin [=F-238], isotianil [=F-239], methasulfocarb [=F-240], metrafenone [=F-250], methyl isothiocyanate [=F-251], mildiomycin [=F-252], natamycin [=F-253], nickel dimethyl dithiocarbamate [=F-254], nitrothal-isopropyl [=F-255], octhilinone [=F-256], oxamocarb [=F-257], oxyfenthiin [=F-258], pentachlorophenol [=F-259] and salts, 2-phenylphenol [=F-260] and salts, piperalin [=F-261], propanosine-sodium [=F-262], proquinazid [=F-263], pyrrolnitrin [=F-264], quintozene [=F-265], tecloftalam [=F-266], tecnazene [=F-267], triazoxide [=F-268], trichlamide [=F-269], zarilamid [=F-270], 2,3,5,6- tetrachloro-4-(methylsulfonyl)pyridine [=F-271], N-(4-chloro-2-nitrophenyl)-N-ethyl-4-methylbenzenesulfonamide [=F-272], 2-amino-4-methyl-N-phenyl-5-thiazolecarboxamide [=F-273], 2-chloro-N-(2,3-dihydro-1,1,3-trimethyl-1H-inden-4-yl)-3-pyridine-icarboxamide [=F-274], 3-[5-(4-chlorophenyl)-2,3-dimethylisoxazolidin-3-yl]pyridine [=F-275], cis-1-(4-chloro¬phenyl)-2-(1H-1,2,4-triazol-1-yl)cyclo-heptanol [=F-276], 2,4-dihydro-5-methoxy-2-methyl-4-[[[[1-[3-(trifluoromethyl)phenyl]ethylidene]amino]¬oxy] methyl]phenyl]-3H-1,2,3-triazol-3-one (185336-79-2) [=F-277], methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxy¬phenyl)imino]methyl]thio]methyl]-alpha-(methoxymethylene)benzacetate [=F-278], 4-chloro-alpha-propynyloxy-N-[2-[3-methoxy-4-(2-propynyloxy)phenyl]ethyl]benz¬acet¬amide [=F-279], (2S)-N-[2-[4-[[3-(4-chlorophenyl)-2-propynyl]oxy]-3-methoxyphenyl]ethyl]-3-methyl-2-[(methylsulfonyl)amino]butanamide [=F-280], 5-chloro-7-(4-methylpiperidin-1-yl)-6-(2,4,6-trifluorophe-nyl)[1,2,4]¬triazolo[1,5-a]pyrimidine [=F-281], 5-chloro-6-(2,4,6-trifluorophenyl)-N-[(1R)-1,2,2-trimethyl-propyl]¬[1,2,4]triazolo[1,5-a]pyrimidine-7-amine, 5-chloro-N-[(1R)-1,2-dimethylpropyl]-6-(2,4,6-trifluoro-phenyl)[1,2,4]triazolo[1,5-a]pyrimidine-7-amine [=F-282], N-[1-(5-bromo-3-chloropyridin-2-yl)ethyl]-2,4-dichloroni-cotinamide [=F-283], N-(5-bromo-3-chloro¬pyridin-2-yl)methyl-2,4-dichloro-nicotinamide [=F-284], 2-butoxy-6-iodo-3-propylbenzopyranon-4-one [=F-285], N-(3-ethyl-3,5,5-trimethylcyclohexyl)-3-formylamino-2-hydroxybenzamide, 2-[[[[1-[3(1-fluoro-2-phenyl¬ethyl)oxy]phenyl]ethylidene]¬amino]oxy]¬methyl]-alpha-(methoxyimino)-N-methyl-alphaE-benzacetamide [=F-286], N-{2-[3-chloro-5-(tri-fluoromethyl)pyridin-2-yl]ethyl}-2-(trifluoro¬methyl)benzamide, N-(3',4'-dichloro-5-fluoro-ibiphenyl-2-yl)-3-(difluoromethyl)-1-methyl-1H-pyrazole-4-carboxamide [=F-287], N-(6-methoxy-3-pyridinyl)cyclopropanecarboxamide, 1-[(4-methoxyphenoxy)methyl]-2,2-dimethylpropyl-1H-imidazole-1-carboxylic acid [=F-288], O-[1-[(4-methoxyphenoxy)methyl]-2,2-dimethylpropyl]-1H-imidazole-1-carbothioic acid [=F-289], 2-(2-{[6-(3-chloro-2-methylphenoxy)-5-fluoropyrimidin-4-yl]oxy}phenyl)-2-(methoxyimino)-N-methyl¬acetamide [=F-290], N-{(Z)-[(cyclopropylmethoxy)¬imino][6-(difluoromethoxy)-2,3-difluorophenyl]¬methyl}-2-benzacetamide [=F-291].

An even more preferred object of present invention, is the combined use of (A1)+(F-1), (A1)+(F-2), (A1)+(F-3), (A1)+(F-4), (A1)+(F-5), (A1)+(F-6), (A1)+(F-7), (A1)+(F-8), (A1)+(F-9), (A1)+(F-10), (A1)+(F-11), (A1)+(F-12), (A1)+(F-13), (A1)+(F-14), (A1)+(F-15), (A1)+(F-16), (A1)+(F-17), (A1)+(F-18), (A1)+(F-19), (A1)+(F-20), (A1)+(F-21), (A1)+(F-22), (A1)+(F-23), (A1)+(F-24), (A1)+(F-25), (A1)+(F-26), (A1)+(F-27), (A1)+(F-28), (A1)+(F-29), (A1)+(F-30), (A1)+(F-31), (A1)+(F-32), (A1)+(F-33), (A1)+(F-34), (A1)+(F-35), (A1)+(F-36), (A1)+(F-37), (A1)+(F-38), (A1)+(F-39), (A1)+(F-40), (A1)+(F-41), (A1)+(F-42), (A1)+(F-43), (A1)+(F-44), (A1)+(F-45), (A1)+(F-46), (A1)+(F-47), (A1)+(F-48), (A1)+(F-49), (A1)+(F-50), (A1)+(F-51), (A1)+(F-52), (A1)+(F-53), (A1)+(F-54), (A1)+(F-55), (A1)+(F-56), (A1)+(F-57), (A1)+(F-58), (A1)+(F-59), (A1)+(F-60), (A1)+(F-61), (A1)+(F-62), (A1)+(F-63), (A1)+(F-64), (A1)+(F-65), (A1)+(F-66), (A1)+(F-67), (A1)+(F-68), (A1)+(F-69), (A1)+(F-70), (A1)+(F-71), (A1)+(F-72), (A1)+(F-73), (A1)+(F-74), (A1)+(F-75), (A1)+(F-76), (A1)+(F-77), (A1)+(F-78), (A1)+(F-79), (A1)+(F-80), (A1)+(F-81), (A1)+(F-82), (A1)+(F-83), (A1)+(F-84), (A1)+(F-85), (A1)+(F-86), (A1)+(F-87), (A1)+(F-88), (A1)+(F-89), (A1)+(F-90), (A1)+(F-91), (A1)+(F-92), (A1)+(F-93), (A1)+(F-94), (A1)+(F-95), (A1)+(F-96), (A1)+(F-97), (A1)+(F-98), (A1)+(F-99), (A1)+(F-100), (A1)+(F-101), (A1)+(F-102), (A1)+(F-103), (A1)+(F-104), (A1)+(F-105), (A1)+(F-106), (A1)+(F-107), (A1)+(F-108), (A1)+(F-109), (A1)+(F-110), (A1)+(F-111), (A1)+(F-112), (A1)+(F-113), (A1)+(F-114), (A1)+(F-115), (A1)+(F-116), (A1)+(F-117), (A1)+(F-118), (A1)+(F-119), (A1)+(F-120), (A1)+(F-121), (A1)+(F-122), (A1)+(F-123), (A1)+(F-124), (A1)+(F-125), (A1)+(F-126), (A1)+(F-127), (A1)+(F-128), (A1)+(F-129), (A1)+(F-130), (A1)+(F-131), (A1)+(F-132), (A1)+(F-133), (A1)+(F-134), (A1)+(F-135), (A1)+(F-136), (A1)+(F-137), (A1)+(F-138), (A1)+(F-139), (A1)+(F-140), (A1)+(F-141), (A1)+(F-142), (A1)+(F-143), (A1)+(F-144), (A1)+(F-145), (A1)+(F-146), (A1)+(F-147), (A1)+(F-148), (A1)+(F-149), (A1)+(F-150), (A1)+(F-151), (A1)+(F-152), (A1)+(F-153), (A1)+(F-154), (A1)+(F-155), (A1)+(F-156), (A1)+(F-157), (A1)+(F-158), (A1)+(F-159), (A1)+(F-160), (A1)+(F-161), (A1)+(F-162), (A1)+(F-163), (A1)+(F-164), (A1)+(F-165), (A1)+(F-166), (A1)+(F-167), (A1)+(F-168), (A1)+(F-169), (A1)+(F-170), (A1)+(F-171), (A1)+(F-172), (A1)+(F-173), (A1)+(F-174), (A1)+(F-175), (A1)+(F-176), (A1)+(F-177), (A1)+(F-178), (A1)+(F-179), (A1)+(F-180), (A1)+(F-181), (A1)+(F-182), (A1)+(F-183), (A1)+(F-184), (A1)+(F-185), (A1)+(F-186), (A1)+(F-187), (A1)+(F-188), (A1)+(F-189), (A1)+(F-190), (A1)+(F-191), (A1)+(F-192), (A1)+(F-193), (A1)+(F-194), (A1)+(F-195), (A1)+(F-196), (A1)+(F-197), (A1)+(F-198), (A1)+(F-199), (A1)+(F-200), (A1)+(F-201), (A1)+(F-202), (A1)+(F-203), (A1)+(F-204), (A1)+(F-205), (A1)+(F-206), (A1)+(F-207), (A1)+(F-208), (A1)+(F-209), (A1)+(F-210), (A1)+(F-211), (A1)+(F-212), (A1)+(F-213), (A1)+(F-214), (A1)+(F-215), (A1)+(F-216), (A1)+(F-217), (A1)+(F-218), (A1)+(F-219), (A1)+(F-220), (A1)+(F-221), (A1)+(F-222), (A1)+(F-223), (A1)+(F-224), (A1)+(F-225), (A1)+(F-226), (A1)+(F-227), (A1)+(F-228), (A1)+(F-229), (A1)+(F-230), (A1)+(F-231), (A1)+(F-232), (A1)+(F-233), (A1)+(F-234), (A1)+(F-235), (A1)+(F-236), (A1)+(F-237), (A1)+(F-238), (A1)+(F-239), (A1)+(F-240), (A1)+(F-241), (A1)+(F-242), (A1)+(F-243), (A1)+(F-244), (A1)+(F-245), (A1)+(F-246), (A1)+(F-247), (A1)+(F-248), (A1)+(F-249), (A1)+(F-250), (A1)+(F-251), (A1)+(F-252), (A1)+(F-253), (A1)+(F-254), (A1)+(F-255), (A1)+(F-256), (A1)+(F-257), (A1)+(F-258), (A1)+(F-259), (A1)+(F-260), (A1)+(F-261), (A1)+(F-262), (A1)+(F-263), (A1)+(F-264), (A1)+(F-265), (A1)+(F-266), (A1)+(F-267), (A1)+(F-268), (A1)+(F-269), (A1)+(F-270), (A1)+(F-271), (A1)+(F-272), (A1)+(F-273), (A1)+(F-274), (A1)+(F-275), (A1)+(F-276), (A1)+(F-277), (A1)+(F-278), (A1)+(F-279), (A1)+(F-280), (A1)+(F-281), (A1)+(F-282), (A1)+(F-283), (A1)+(F-284), (A1)+(F-285), (A1)+(F-286), (A1)+(F-287), (A1)+(F-288), (A1)+(F-289), (A1)+(F-290), or
(A1)+(F-291),
for inducing specific growth regulating responses on plants, on seeds from which they grow and/or on the locus in which they grow in their normal habitat, preferably in the absence of extraordinary environmental conditions and, thereby, increasing the yield in such treated plants.

The above defined plant yield increasing combinations are not yet known in the art, per se.

Therefore, plant yield increasing compositions comprising such above defined combinations are also an object of present invention.

An even more preferred object of present invention is the combined use of Compound (A), specifically compound (A1), and one or more, preferably one or two fungicides selected from the group consisiting of:

bixafen [=F-26], fluopyram [=F-31], penflufen [=F-36], isopyrazam [F-40], sedaxane [=F41], 3-(difluoromethyl)-1-methyl-N-(3',4',5'-trifluorobiphenyl-2-yl)-1H-pyrazole-4-carboxamide [=F-42], azoxystrobin [F-47], fluoxastrobin [=F-53], pyraclostrobin [F-57], trifloxystrobin [=F-60], epoxiconazole [=F-108], metconazole [=F-119], propiconazole [=F-123], prothioconazole [=F-124], tebuconazole [=F-127], for inducing specific growth regulating responses on plants, on seeds from which they grow and/or on the locus in which they grow in their normal habitat, preferably in the absence of extraordinary environmental conditions and, thereby, increasing the yield in such treated plants.

An even more preferred object of present invention is the combined use of (A1)+(F-26), (A1)+(F31), (A1)+(F-36), (A1)+(F-40), (A1)+(F-41), (A1)+(F-42), (A1)+(F-47), (A1)+(F-53), (A1)+(F-57), (A1)+(F-60), (A1)+(F-108), (A1)+(F-119), (A1)+(F-123), (A1)+(F-124), (A1)+(F-127), (A1)+(F-26)+(F31), (A1)+(F-26)+(F-36), (A1)+(F-26)+(F-40), (A1)+(F-26)+(F-41), (A1)+(F-26)+(F-42), (A1)+(F-26)+(F-47), (A1)+(F-26)+(F-53), (A1)+(F-26)+(F-57), (A1)+(F-26)+(F-60), (A1)+(F-26)+(F-108), (A1)+(F-26)+(F-119), (A1)+(F-26)+(F-123), (A1)+(F-26)+(F-124), (A1)+(F-26)+(F-127), (A1)+(F-36)+(F-40), (A1)+(F-36)+(F-41), (A1)+(F-36)+(F-42), (A1)+(F-36)+(F-47), (A1)+(F-36)+(F-53), (A1)+(F-36)+(F-57), (A1)+(F-36)+(F-60), (A1)+(F-36)+(F-108), (A1)+(F-36)+(F-119), (A1)+(F-36)+(F-123), (A1)+(F-36)+(F-124), (A1)+(F-36)+(F-127), (A1)+(F-40)+(F-41), (A1)+(F-40)+(F-42), (A1)+(F-40)+(F-47), (A1)+(F-40)+(F-53), (A1)+(F-40)+(F-57), (A1)+(F-40)+(F-60), (A1)+(F-40)+(F-108), (A1)+(F-40)+(F-119), (A1)+(F-40)+(F-123), (A1)+(F-40)+(F-124), (A1)+(F-40)+(F-127), (A1)+(F-41)+(F-42), (A1)+(F-41)+(F-47), (A1)+(F-41)+(F-53), (A1)+(F-41)+(F-57), (A1)+(F-41)+(F-60), (A1)+(F-41)+(F-108), (A1)+(F-41)+(F-119), (A1)+(F-41)+(F-123), (A1)+(F-41)+(F-124), (A1)+(F-41)+(F-127), (A1)+(F-42)+(F-53), (A1)+(F-42)+(F-57), (A1)+(F-42)+(F-60), (A1)+(F-42)+(F-108), (A1)+(F-42)+(F-1 19), (A1)+(F-42)+(F-123), (A1)+(F-42)+(F-124), (A1)+(F-42)+(F-127), (A1)+(F-47)+(F-53), (A1)+(F-47)+(F-57), (A1)+(F-47)+(F-60), (A1)+(F-47)+(F-108), (A1)+(F-47)+(F-1 19), (A1)+(F-47)+(F-123), (A1)+(F-47)+(F-124), or (A1)+(F-47)+(F-127), (A1)+(F-53)+(F-57), (A1)+(F-53)+(F-60), (A1)+(F-53)+(F-108), (A1)+(F-53)+(F-119), (A1)+(F-53)+(F-123),(A1)+(F-53)+(F-124), (A1)+(F-53)+(F-127), (A1)+(F-57)+(F-60), (A1)+(F-57)+(F-108), (A1)+(F-57)+(F-119), (A1)+(F-57)+(F-123), (A1)+(F-57)+(F-124), (A1)+(F-57)+(F-127), (A1)+(F-60)+(F-108), (A1)+(F-60)+(F-119), (A1)+(F-60)+(F-123), (A1)+(F-60)+(F-124), or (A1)+(F-60)+(F-127), (A1)+(F-108)+(F-119), (A1)+(F-108)+(F-123), (A1)+(F-108)+(F-124), (A1)+(F-108)+(F-127), (A1)+(F-119)+(F-123), (A1)+(F-119)+(F-124), (A1)+(F-119)+(F-127), (A1)+(F-123)+(F-124), (A1)+(F-123)+(F-127), or (A1)+(F-124)+(F-127), for inducing specific growth regulating responses on plants, on seeds from which they grow and/or on the locus in which they grow in their normal habitat, preferably in the absence of extraordinary environmental conditions and, thereby, increasing the yield in such treated plants.

An even more preferred object of present invention is the combined use of (A1)+(F-108), (A1)+(F-26)+(F-124), (A1)+(F-26)+(F-127), (A1)+(F-42)+(F-124), (A1)+(F-53)+(F-124), (A1)+(F-57)+(F-119), (A1)+(F-57)+(F-124), (A1)+(F-60)+(F-123), (A1)+(F-60)+(F-124), or (A1)+(F-124)+(F-127), for inducing specific growth regulating responses on plants, on seeds from which they grow and/or on the locus in which they grow in their normal habitat, preferably in the absence of extraordinary environmental conditions and, thereby, increasing the yield in such treated plants.

An even more preferred object of present invention is the combined use of (A1)+(F-108), (A1)+(F-60)+(F-124), or (A1)+(F-124)+(F-127), for inducing specific growth regulating responses on plants, on seeds from which they grow and/or on the locus in which they grow in their normal habitat, preferably in the absence of extraordinary environmental conditions and, thereby, increasing the yield in such treated plants.

Plant yield increasing compositions comprising
(A1)+(F-3), (A1)+(F-4), (A1)+(F-5), (A1)+(F-6), (A1)+(F-7), (A1)+(F-9), (A1)+(F-12), (A1)+(F-14), (A1)+(F-15), (A1)+(F-18), (A1)+(F-19), (A1)+(F-21), (A1)+(F-24), (A1)+(F-25), (A1)+(F-26), (A1)+(F-28), (A1)+(F-29), (A1)+(F-30), (A1)+(F-31), (A1)+(F-32), (A1)+(F-33), (A1)+(F-34), (A1)+(F-35), (A1)+(F-36), (A1)+(F-38), (A1)+(F-39), (A1)+(F-40), (A1)+(F-41), (A1)+(F-42), (A1)+(F-43), (A1)+(F-44), (A1)+(F-45), (A1)+(F-46), (A1)+(F-50), (A1)+(F-56), (A1)+(F-58), (A1)+(F-62), (A1)+(F-65), (A1)+(F-67), (A1)+(F-68), (A1)+(F-69), (A1)+(F-71), (A1)+(F-72), (A1)+(F-73), (A1)+(F-74), (A1)+(F-75), (A1)+(F-76), (A1)+(F-78), (A1)+(F-79), (A1)+(F-82), (A1)+(F-84), (A1)+(F-85), (A1)+(F-86), (A1)+(F-88), (A1)+(F-89), (A1)+(F-90), (A1)+(F-91), (A1)+(F-92), (A1)+(F-93), (A1)+(F-94), (A1)+(F-95), (A1)+(F-96), (A1)+(F-97), (A1)+(F-101), (A1)+(F-103), (A1)+(F-104), (A1)+(F-106), (A1)+(F-107), (A1)+(F-108), (A1)+(F-109), (A1)+(F-110), (A1)+(F-113), (A1)+(F-114), (A1)+(F-115), (A1)+(F-117), (A1)+(F-118), (A1)+(F-121), (A1)+(F-125), (A1)+(F-130), (A1)+(F-131), (A1)+(F-132), (A1)+(F-133), (A1)+(F-134), (A1)+(F-135), (A1)+(F-136), (A1)+(F-137), (A1)+(F-138), (A1)+(F-139), (A1)+(F-140), (A1)+(F-141), (A1)+(F-143), (A1)+(F-144), (A1)+(F-145), (A1)+(F-146), (A1)+(F-147), (A1)+(F-149), (A1)+(F-150), (A1)+(F-151), (A1)+(F-152), (A1)+(F-153), (A1)+(F-154), (A1)+(F-155), (A1)+(F-156), (A1)+(F-157), (A1)+(F-158), (A1)+(F-160), (A1)+(F-161), (A1)+(F-162), (A1)+(F-164), (A1)+(F-165), (A1)+(F-166), (A1)+(F-168), (A1)+(F-169), (A1)+(F-170), (A1)+(F-171), (A1)+(F-172), (A1)+(F-173), (A1)+(F-174), (A1)+(F-175), (A1)+(F-176), (A1)+(F-177), (A1)+(F-180), (A1)+(F-181), (A1)+(F-183), (A1)+(F-184), (A1)+(F-185), (A1)+(F-186), (A1)+(F-188), (A1)+(F-190), (A1)+(F-191), (A1)+(F-193), (A1)+(F-195), (A1)+(F-196), (A1)+(F-197), (A1)+(F-199), (A1)+(F-202), (A1)+(F-203), (A1)+(F-205), (A1)+(F-209), (A1)+(F-210), (A1)+(F-211), (A1)+(F-212), (A1)+(F-213), (A1)+(F-214), (A1)+(F-215), (A1)+(F-216), (A1)+(F-217), (A1)+(F-218), (A1)+(F-220), (A1)+(F-221), (A1)+(F-222), (A1)+(F-223), (A1)+(F-224), (A1)+(F-225), (A1)+(F-226), (A1)+(F-227), (A1)+(F-

229), (A1)+(F-230), (A1)+(F-231), (A1)+(F-232), (A1)+(F-233), (A1)+(F-234), (A1)+(F-235), (A1)+(F-236), (A1)+(F-238), (A1)+(F-239), (A1)+(F-240), (A1)+(F-241), (A1)+(F-242), (A1)+(F-243), (A1)+(F-244), (A1)+(F-245), (A1)+(F-246), (A1)+(F-247), (A1)+(F-248), (A1)+(F-249), (A1)+(F-250), (A1)+(F-251), (A1)+(F-252), (A1)+(F-253), (A1)+(F-254), (A1)+(F-255), (A1)+(F-256), (A1)+(F-257), (A1)+(F-258), (A1)+(F-259), (A1)+(F-260), (A1)+(F-261), (A1)+(F-262), (A1)+(F-263), (A1)+(F-264), (A1)+(F-265), (A1)+(F-266), (A1)+(F-267), (A1)+(F-269), (A1)+(F-270), (A1)+(F-271), (A1)+(F-272), (A1)+(F-273), (A1)+(F-274), (A1)+(F-275), (A1)+(F-276), (A1)+(F-277), (A1)+(F-278), (A1)+(F-279), (A1)+(F-280), (A1)+(F-281), (A1)+(F-282), (A1)+(F-283), (A1)+(F-284), (A1)+(F-286), (A1)+(F-288), (A1)+(F-289), (A1)+(F-290), (A1)+(F-291), (A1)+(F-26)+(F31), (A1)+(F-26)+(F-36), (A1)+(F-26)+(F-40), (A1)+(F-26)+(F-41), (A1)+(F-26)+(F-42), (A1)+(F-26)+(F-47), (A1)+(F-26)+(F-53), (A1)+(F-26)+(F-57), (A1)+(F-26)+(F-60), (A1)+(F-26)+(F-108), (A1)+(F-26)+(F-119), (A1)+(F-26)+(F-123), (A1)+(F-26)+(F-124), (A1)+(F-26)+(F-127);

(A1)+(F-36)+(F-40), (A1)+(F-36)+(F-41), (A1)+(F-36)+(F-42), (A1)+(F-36)+(F-47), (A1)+(F-36)+(F-53), (A1)+(F-36)+(F-57), (A1)+(F-36)+(F-60), (A1)+(F-36)+(F-108), (A1)+(F-36)+(F-119), (A1)+(F-36)+(F-123), (A1)+(F-36)+(F-124), (A1)+(F-36)+(F-127), (A1)+(F-40)+(F-41), (A1)+(F-40)+(F-42), (A1)+(F-40)+(F-47), (A1)+(F-40)+(F-53), (A1)+(F-40)+(F-57), (A1)+(F-40)+(F-60), (A1)+(F-40)+(F-108), (A1)+(F-40)+(F-119), (A1)+(F-40)+(F-123), (A1)+(F-40)+(F-124), or (A1)+(F-40)+(F-127);

(A1)+(F-41)+(F-42), (A1)+(F-41)+(F-47), (A1)+(F-41)+(F-53), (A1)+(F-41)+(F-57), (A1)+(F-41)+(F-60), (A1)+(F-41)+(F-108), (A1)+(F-41)+(F-119), (A1)+(F-41)+(F-123), (A1)+(F-41)+(F-124), (A1)+(F-41)+(F-127), (A1)+(F-42)+(F-53), (A1)+(F-42)+(F-57), (A1)+(F-42)+(F-60), (A1)+(F-42)+(F-108), (A1)+(F-42)+(F-1 19), (A1)+(F-42)+(F-123), (A1)+(F-42)+(F-124), (A1)+(F-42)+(F-127), (A1)+(F-47)+(F-53), (A1)+(F-47)+(F-57), (A1)+(F-47)+(F-60), (A1)+(F-47)+(F-108), (A1)+(F-47)+(F-1 19), (A1)+(F-47)+(F-123), (A1)+(F-47)+(F-124), (A1)+(F-47)+(F-127), (A1)+(F-53)+(F-57), (A1)+(F-53)+(F-60), (A1)+(F-53)+(F-108), (A1)+(F-53)+(F-119), (A1)+(F-53)+(F-123), (A1)+(F-53)+(F-124), (A1)+(F-53)+(F-127), (A1)+(F-57)+(F-60), (A1)+(F-57)+(F-108), (A1)+(F-57)+(F-119), (A1)+(F-57)+(F-123), (A1)+(F-57)+(F-124), (A1)+(F-57)+(F-127);

(A1)+(F-60)+(F-108), (A1)+(F-60)+(F-119), (A1)+(F-60)+(F-123), (A1)+(F-60)+(F-124), (A1)+(F-60)+(F-127), (A1)+(F-108)+(F-119), (A1)+(F-108)+(F-123),(A1)+(F-108)+(F-124), (A1)+(F-108)+(F-127), (A1)+(F-119)+(F-123), (A1)+(F-119)+(F-124), (A1)+(F-119)+(F-127);

(A1)+(F-123)+(F-124), (A1)+(F-123)+(F-127), or (A1)+(F-124)+(F-127)

are not yet known in the art.

Therefore, above defined plant yield increasing compositions, preferably those comprising as mixture partners to Compound (A1) a combination selected from the group consisting of (i) pyraclostrobin (F-57) and metconazole (F-119), (ii) trifloxystrobin (F-60) and propiconazole (F-123), (iii) prothioconazole (F-124) and tebuconazole (F-127), (iv) fluoxastrobin (F-53) and prothioconazole (F-124), and (v) trifloxystrobin (F-60) and prothioconazole (F-124), (vi) bixafen (F-26) and prothioconazole (F-124), (vii) bixafen (F-26) and tebuconazole (F127), (viii) bixafen (F-26) and trifloxystrobin (F-60), more preferably those comprising as mixture partners to Compound (A1) a combination selected from the group consisting of, (i) pyraclostrobin (F-57) and metconazole (F-119), (ii) trifloxystrobin (F-60) and propiconazole (F-123), (iii) bixafen (F-26) and prothioconazole (F-124), are also a a further preferred object of the present invention.

Also more specifically, the insecticides to be combined with Compound (A), specifically Compound (A1), are selected from the group consisiting of:

abamectin [=I-1], chlorpyrifos [=I-2], clothianidin [=I-3], cyazypyr [=I-4], deltamethrin [=I-5], emamectin-benzoate [=I-6], ethiprole [=I-7], fipronil [=I-8], flubendiamide [=I-9], flupyradifurone [=I-10], imidacloprid [=I-11], lambda-cyhalothrin [=I-12], lufenuron [=I-13], rynaxypyr [=I-14], spinosad [=I-15], spinoteram [=I-16], spirotetramate [=I-17], sulfoxaflor [=I-18], thiamethoxam [=I-19], thiodicarb [=I-20], triflumuron [=I-21], votivo [=I-22].

An even more preferred object of present invention, is the combined use of (A1)+(I-1), (A1)+(I-2), (A1)+(I-3), (A1)+(I-4), (A1)+(I-5), (A1)+(I-6) (A1)+(I-7), (A1)+(I-8), (A1)+(I-9), (A1)+(I-10), (A1)+(I-11), (A1)+(I-12) (A1)+(I-13), (A1)+(I-14), (A1)+(I-15), (A1)+(I-16), (A1)+(I-17), (A1)+(I-18) (A1)+(I-19), (A1)+(I-20), (A1)+(I-3), or (A1)+(I-21), (A1)+(I-22), for inducing specific growth regulating responses on plants, on seeds from which they grow or on the locus in which they grow in their normal habitat, preferably in the absence of extraordinary environmental conditions and, thereby, increasing the yield in such treated plants.

Even more specifically, the combination partners concerning the class of insecticides are selected from the group consisiting of:

abamectin [=I-1], chlorpyrifos [=I-2], clothianidin [=I-3], fipronil [=I-8], flupyradifurone [=I-10], imidacloprid [=I-11], lambda-cyhalothrin [=I-12], lufenuron [=I-13], rynaxypyr [=I-14], spinoteram [=I-16], spirotetramate [=I-17], sulfoxaflor [=I-18], thiamethoxam [I=19], thiodicarb [=I-20], votivo [=I-22]

for inducing specific growth regulating responses on plants, on seeds from which they grow and/or on the locus in which they grow in their normal habitat, preferably in the absence of extraordinary environmental conditions and, thereby, increasing the yield in such treated plants.

An even more preferred object of present invention is the combined use of (A1)+(I-1)+(I-2), (A1)+(I-1)+(I-3), (A1)+(I-1)+(I-8), (A1)+(I-1)+(I-10), (A1)+(I-1)+(I-11), (A1)+(I-1)+(I-12), (A1)+(I-1)+(I-13), (A1)+(I-1)+(I-14), (A1)+(I-1)+(I-16), (A1)+(I-1)+(I-17), (A1)+(I-1)+(I-18), (A1)+(I-1)+(I-19), (A1)+(I-1)+(I-20), (A1)+(I-1)+(I-22), (A1)+(I-2)+(I-3), (A1)+(I-2)+(I-8), (A1)+(I-2)+(I-10), (A1)+(I-2)+(I-11), (A1)+(I-2)+(I-12), (A1)+(I-2)+(I-13), (A1)+(I-2)+(I-14), (A1)+(I-2)+(I-16), (A1)+(I-2)+(I-17), (A1)+(I-2)+(I-18), (A1)+(I-2)+(I-19), (A1)+(I-2)+(I-20), (A1)+(I-2)+(I-22), (A1)+(I-3)+(I-8), (A1)+(I-3)+(I-10), (A1)+(I-3)+(I-11), (A1)+(I-3)+(I-12), (A1)+(I-3)+(I-13), (A1)+(I-3)+(I-14), (A1)+(I-3)+(I-16), (A1)+(I-3)+(I-17), (A1)+(I-3)+(I-18), (A1)+(I-3)+(I-19), (A1)+(I-3)+(I-20), (A1)+(I-3)+(I-22), (A1)+(I-8)+(I-10), (A1)+(I-8)+(I-11), (A1)+(I-8)+(I-12), (A1)+(I-8)+(I-13), (A1)+(I-8)+(I-14), (A1)+(I-8)+(I-16), (A1)+(I-8)+(I-17), (A1)+(I-8)+(I-18), (A1)+(I-8)+(I-19), (A1)+(I-8)+(I-20), (A1)+(I-8)+(I-22), (A1)+(I-10)+(I-11), (A1)+(I-10)+(I-12), (A1)+(I-10)+(I-13), (A1)+(I-10)+(I-14), (A1)+(I-10)+(I-16), (A1)+(I-10)+(I-17), (A1)+(I-10)+(I-18), (A1)+(I-10)+(I-19), (A1)+(I-10)+(I-20), (A1)+(I-10)+(I-22), (A1)+(I-11)+(I-12), (A1)+(I-11)+(I-13), (A1)+(I-11)+(I-14), (A1)+(I-11)+(I-16), (A1)+(I-11)+(I-17), (A1)+(I-11)+(I-18), (A1)+(I-11)+(I-19), (A1)+(I-11)+(I-20), (A1)+(I-11)+(I-22), (A1)+(I-12)+(I-13), (A1)+(I-12)+(I-14), (A1)+(I-12)+(I-16), (A1)+(I-12)+(I-17), (A1)+(I-12)+(I-18), (A1)+(I-12)+(I-19), (A1)+(I-12)+(I-20), (A1)+(I-12)+(I-22), (A1)+(I-13)+(I-14), (A1)+(I-13)+(I-16), (A1)+(I-13)+(I-17), (A1)+(I-13)+(I-18), (A1)+(I-13)+(I-19), (A1)+(I-13)+(I-20), (A1)+(I-13)+(I-22), (A1)+(I-14)+(I-16), (A1)+(I-14)+(I-17), (A1)+(I-14)+(I-18), (A1)+(I-14)+(I-19), (A1)+(I-14)+(I-20), (A1)+(I-14)+(I-22), (A1)+(I-16)+(I-17), (A1)+(I-16)+(I-18), (A1)+(I-16)+(I-19), (A1)+(I-16)+(I-20), (A1)+(I-16)+(I-22), (A1)+(I-17)+(I-18), (A1)+(I-17)+(I-19), (A1)+(I-17)+(I-20), (A1)+(I-17)+(I-22), (A1)+(I-18)+(I-19), (A1)+(I-18)+(I-20), (A1)+(I-18)+(I-22), (A1)+(I-19)+(I-20), (A1)+(I-19)+(I-22), or (A1)+(I-20)+(I-22), for inducing specific growth regulating responses on plants, on seeds from which they grow and/or on the locus in which they grow in their normal habitat, preferably in the absence of extraordinary environmental conditions and, thereby, increasing the yield in such treated plants.

Plant yield increasing compositons comprising (A1)+(I-1)+(I-2), (A1)+(I-1)+(I-3), (A1)+(I-1)+(I-8), (A1)+(I-1)+(I-10), (A1)+(I-1)+(I-11), (A1)+(I-1)+(I-12), (A1)+(I-1)+(I-13), (A1)+(I-1)+(I-14), (A1)+(I-1)+(I-16), (A1)+(I-1)+(17), (A1)+(I-1)+(I-18), (A1)+(I-1)+(I-20), (A1)+(I-1)+(I-22), (A1)+(I-2)+(I-3), (A1)+(I-2)+(I-8), (A1)+(I-2)+(I-10), (A1)+(I-2)+(I-11), (A1)+(I-2)+(I-12), (A1)+(I-2)+(I-13), (A1)+(I-2)+(I-14), (A1)+(I-2)+(I-16), (A1)+(I-2)+(I-17), (A1)+(I-2)+(I-18), (A1)+(I-1)+(I-19), (A1)+(I-2)+(I-20), (A1)+(I-2)+(I-22), (A1)+(I-3)+(I-8), (A1)+(I-3)+(I-10), (A1)+(I-3)+(I-12), (A1)+(I-3)+(I-13), (A1)+(I-3)+(I-14), (A1)+(I-3)+(I-16), (A1)+(I-3)+(I-17), (A1)+(I-3)+(I-18), (A1)+(I-3)+(I-20), (A1)+(I-3)+(I-22), (A1)+(I-8)+(I-10), (A1)+(I-8)+(I-11), (A1)+(I-8)+(I-12), (A1)+(I-8)+(I-13), (A1)+(I-8)+(I-14), (A1)+(I-8)+(I-16), (A1)+(I-8)+(I-17), (A1)+(I-8)+(I-18), (A1)+(I-8)+(I-19), (A1)+(I-8)+(I-20), (A1)+(I-8)+(I-22), (A1)+(I-10)+(I-11), (A1)+(I-10)+(I-12), (A1)+(I-10)+(I-13), (A1)+(I-10)+(I-14), (A1)+(I-10)+(I-16), (A1)+(I-10)+(17), (A1)+(I-10)+(I-18), (A1)+(I-10)+(I-19), (A1)+(I-10)+(I-20), (A1)+(I-10)+(I-22), (A1)+(I-11)+(I-12), (A1)+(I-11)+(I-13), (A1)+(I-11)+(I-14), (A1)+(I-11)+(I-16), (A1)+(I-11)+(I-17), (A1)+(I-11)+(I-18), (A1)+(I-11)+(I-20), (A1)+(I-11)+(I-22), (A1)+(I-12)+(I-13), (A1)+(I-12)+(I-14), (A1)+(I-12)+(I-16), (A1)+(I-12)+(I-17), (A1)+(I-12)+(I-18), (A1)+(I-12)+(I-19), (A1)+(I-12)+(I-20), (A1)+(I-12)+(I-22), (A1)+(I-13)+(I-14), (A1)+(I-13)+(I-16), (A1)+(I-13)+(17), (A1)+(I-13)+(I-18), (A1)+(I-13)+(I-20), (A1)+(I-13)+(I-22), (A1)+(I-14)+(I-16), (A1)+(I-14)+(I-17), (A1)+(I-14)+(I-18), (A1)+(I-14)+(I-19), (A1)+(I-14)+(I-20), (A1)+(I-14)+(I-22), (A1)+(I-16)+(I-17), (A1)+(I-16)+(I-18), (A1)+(I-16)+(I-19), (A1)+(I-16)+(I-20), (A1)+(I-16)+(I-22), (A1)+(I-17)+(I-18), (A1)+(I-17)+(I-19), (A1)+(I-17)+(I-20), (A1)+(I-17)+(I-22), (A1)+(I-18)+(I-19), (A1)+(I-18)+(I-20), (A1)+(I-18)+(I-22), (A1)+(I-19)+(I-20), (A1)+(I-19)+(I-22), or (A1)+(I-20)+(I-22), are not yet known in the art.

Therefore, above defined compositions are also a further object of the present invention.

Also more specifically, the plant growth regulators to be combined with Compound (A) or Compound (A1) according to present invention, preferably to be combined with Compound (A1), are selected from the group consisiting of: Chlormequat-chloride (CCC) [=PGR-1], ethephon [=PGR-2], mepiquat [=PGR-3], trinexapac-ethyl [=PGR-4], 2,4-D (=PGR-5), MCPA (=PGR-6) and 2,4-D Choline (=PGR-7)

A further preferred object of present invention, is the combined use of (A1)+(PGR-1), (A1)+(PGR-2), (A1)+PGR-3), (A1)+(PGR-4), (A1)+(PGR-5), (A1)+(PGR-6), (A1)+(PGR-7), (A1)+(PGR-1)+(PGR-2), (A1)+(PGR-1)+(PGR-3), (A1)+(PGR-1)+(PGR-4), (A1)+(PGR-1)+(PGR-5), (A1)+(PGR-1)+(PGR-6), (A1)+(PGR-1)+(PGR-7), (A1)+(PGR-2)+(PGR-3), (A1)+(PGR-2)+(PGR-4), (A1)+(PGR-2)+(PGR-4), (A1)+(PGR-2)+(PGR-5), (A1)+(PGR-2)+(PGR-6), (A1)+(PGR-2)+(PGR-7), (A1)+(PGR-3)+(PGR-4), (A1)+(PGR-3)+(PGR-5), (A1)+(PGR-3)+(PGR-6), (A1)+(PGR-3)+(PGR-7), (A1)+(PGR-4)+(PGR-5), (A1)+(PGR-4)+(PGR-6), (A1)+(PGR-4)+(PGR-7), (A1)+(PGR-5)+(PGR-6), (A1)+(PGR-5)+(PGR-7), or (A1)+(PGR-6)+(PGR-7), for inducing specific growth regulating responses on plants, on seeds from which they grow or on the locus in which they grow in their normal habitat, preferably in the absence of extraordinary environmental conditions and, thereby, increasing the yield in such treated plants.

An even more preferred object of present invention is the combined use of (A1)+(PGR-5)+(PGR6).

Plant yield increasing compositions comprising (A1)+(PGR-1), (A1)+(PGR-2), (A1)+PGR-3), (A1)+(PGR-4), (A1)+(PGR-5), (A1)+(PGR-6), (A1)+(PGR-7), (A1)+(PGR-1)+(PGR-2), (A1)+(PGR-1)+(PGR-3), (A1)+(PGR-1)+(PGR-4), (A1)+(PGR-1)+(PGR-5), (A1)+(PGR-1)+(PGR-6), (A1)+(PGR-1)+(PGR-7), (A1)+(PGR-2)+(PGR-3), (A1)+(PGR-2)+(PGR-4), (A1)+(PGR-2)+(PGR-4), (A1)+(PGR-2)+(PGR-5), (A1)+(PGR-2)+(PGR-6), (A1)+(PGR-2)+(PGR-7), (A1)+(PGR-3)+(PGR-4), (A1)+(PGR-3)+(PGR-5), (A1)+(PGR-3)+(PGR-6), (A1)+(PGR-3)+(PGR-7).

(A1)+(PGR-4)+(PGR-5), (A1)+(PGR-4)+(PGR-6), (A1)+(PGR-4)+(PGR-7)

(A1)+(PGR-5)+(PGR-6), (A1)+(PGR-5)+(PGR-7), or (A1)+(PGR-6)+(PGR-7)

are not yet known in the art.

Therefore, such above defined combinations are also a further object of the present invention.

It is to be said that, even by claiming the preferred use of the above defined combinations of Compounds (A), preferably Compound (A1), with one or more compound(s) selected from the agrochemical compounds in the absence of extraordinary environmental stress conditions, the combined application might also be useful in cases where such extraordinary environmental stress conditions do exist for a certain time period, or, preferably, in an interim phase, i.e. phases in which no extraordinary environmental stress conditions do exist are interrupted by one or more phases in which extraordinary environmental conditions of identical or different kind do occur.

More specifically, the use of Compound (A), preferably Compound (A1), in combination with one or more agrochemical compound(s), preferably with agrochemical compounds selected from the group of fungicides, insecticides, and plant-growth regulators, doesn't show non-expected effects on plants concerning yield increase only in the absence of extraordinary environmental stress, but also on plants that are exposed to longer periods, preferably weeks, more preferably days of extraordinary environmental stress conditions, preferably heat and/or drought stress.

In accordance with the invention, it has additionally been found that the application, to plants or in their environment, of , of Compounds (A), preferably Compound (A1), either alone or in combination with other agrochemical compounds, especially with those that are above defined as the preferred ones from the group consisting of funigicides, insecticides, and plant growth regulators in combination with at least one fertilizer as defined below is/are possible.

Fertilizers which can be used in accordance with the invention together with the Compounds (A), preferably Compound (A1). either alone or in combination with other agrochemical compounds, especially with those that are above defined as the preferred ones from the group consisting of funigicides, insecticides, and plant growth regulators elucidated in detail above are generally organic and inorganic nitrogen-containing compounds, for example ureas, urea/formaldehyde condensation products, amino acids, ammonium salts and ammonium nitrates, potassium salts (preferably chlorides, sulfates, nitrates), salts of phosphoric acid and/or salts of phosphorous acid (preferably potassium salts and ammonium salts). In this context, particular mention should be made of the NPK fertilizers, i.e. fertilizers which contain nitrogen, phosphorus and potassium, calcium ammonium nitrate, i.e. fertilizers which additionally contain calcium, or ammonium nitrate sulfate (formula $(NH_4)_2SO_4$ $NH_4NO_3$), ammonium phosphate and ammonium sulfate. These fertilizers are generally known to the person skilled in the art; see also, for example, Ullmann's Encyclopedia of Industrial Chemistry, 5th edition, vol. A 10, pages 323 to 431, Verlagsgesellschaft, Weinheim, 1987.

The fertilizers may also contain salts of micronutrients (preferably calcium, sulfur, boron, manganese, magnesium, iron, boron, copper, zinc, molybdenum and cobalt) and phytohormones (for example vitamin B1 and indole-3-acetic acid) or mixtures thereof. Fertilizers used in accordance with the invention may also contain further salts, such as monoammonium phosphate (MAP), diammonium phosphate (DAP), potassium sulfate, potassium chloride, magnesium sulfate. Suitable amounts of the secondary nutrients, or trace elements, are amounts of 0.5 to 5% by weight, based on the overall fertilizer. Further possible ingredients are crop protection compositions, insecticides or fungicides, growth regulators or mixtures thereof. This will be explained in more detail below.

The fertilizers can be used, for example, in the form of powders, granules, prills or compactates. However, the fertilizers can also be used in liquid form, dissolved in an aqueous medium. In this case, it is also possible to use dilute aqueous ammonia as the nitrogen fertilizer. Further possible constituents of fertilizers are described, for example, in Ullmann's Encyclopedia of Industrial Chemistry, 5th edition, 1987, Vol. A 10, pages 363 to 401, DE-A 41 28 828, DE-A 19 05 834 and DE-A 196 31 764. The general composition of the fertilizers which, in the context of the present invention, may take the form of straight and/or compound fertilizers, for example composed of nitrogen, potassium or phosphorus, may vary within a wide range. In general, a content of 1 to 30% by weight of nitrogen (preferably 5 to 20% by weight), 1 to 20% by weight of potassium (preferably 3 to 15% by weight) and a content of 1 to 20% by weight of phosphorus (preferably 3 to 10% by weight) is advantageous. The microelement content is typically in the ppm range, preferably in the range from 1 to 1000 ppm.

In the context of the present invention, the fertilizer and Compounds (A), preferably Compound (A1), either alone or in combination with other agrochemical compounds, especially with those that are above defined as the preferred ones from the group consisting of funigicides, insecticides, and plant growth regulators may be administered simultaneously, i.e. synchronously. However, it is also possible first to apply the fertilizer and then Compounds (A), preferably Compound (A1), either alone or in combination with other agrochemical compounds, especially with those that are above defined as the preferred ones from the group consisting of funigicides, insecticides, and plant growth regulators, or first to apply Compounds (A), preferably Compound (A1), either alone or in combination with other agrochemical compounds, especially with those that are above defined as the preferred ones from the group consisting of funigicides, insecticides, and plant growth regulators, and then the fertilizer. In the case of nonsynchronous application of Compounds (A), preferably Compound (A1), either alone or in combination with other agrochemical compounds, especially with those that are above defined as the preferred ones from the group consisting of funigicides, insecticides, and plant growth regulators, and the fertilizer, the application in the context of the present invention is, however, effected in a functional relationship, especially within a period of generally 24 hours, preferably 18 hours, more preferably 12 hours, specifically 6 hours, more specifically 4 hours, even more specifically within 2 hours. In very particular embodiments of the present invention, Compounds (A), preferably Compound (A1), either alone or in combination with other agrochemical compounds, especially with those that are above defined as the preferred ones from the group consisting of funigicides, insecticides, and plant growth regulators and the fertilizer are applied within a time frame of less than 1 hour, preferably less than 30 minutes, more preferably less than 15 minutes.

The active ingredients for use in accordance with the invention can be employed in the following plants, for example, the enumeration which follows being nonlimiting.

The term "useful plants" as used here refers to crop plants which are employed as plants for obtaining foods, animal feeds, fuels or for industrial purposes, also including ornamentals, turfs, commonly used trees employed as ornamentals in the public and domestic sectors, and forestry trees. Forestry trees include trees for the production of timber, cellulose, paper and products made from parts of the trees.

The useful plants include, for example, the following types of plants: cereals, for example wheat, barley, rye, triticale, durum (hard wheat), oats, hops, rice, corn, millet/sorghum and maize; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cacao beans and peanuts; cucurbits, for example pumpkin/squash, cucumbers and melons; fiber plants, for example cotton, flax, hemp and jute; citrus fruit, for example oranges, lemons, grapefruit and tangerines; vegetables, for example spinach, lettuce, asparagus, cabbage species, carrots, onions, tomatoes, potatoes and bell peppers; Lauraceae, for example avocado, Cinnamonum, camphor, or also plants such as tobacco, nuts, coffee, eggplant, sugarcane, tea, pepper, vine, grapevines, hops, bananas, latex plants, ornamentals, for example flowers, shrubs, deciduous trees and coniferous trees, and plants for turf and lawn. This enumeration does not constitute a limitation.

The following plants are considered to be particularly suitable target crops for the inventive use or method: oats, rye, triticale, durum, cotton, eggplant, turf, pome fruit, stone fruit, soft fruit, corn, wheat, barley, cucumber, tobacco, vines, rice, cereals, pear, pepper, beans, soybeans, oilseed rape, tomato, bell pepper, melons, cabbage, potatoes and apples.

Examples of trees which can be improved in accordance with the inventive method include: *Abies* sp., *Eucalyptus* sp., *Picea* sp., *Pinus* sp., *Aesculus* sp., *Platanus* sp., *Tilia* sp., *Acer* sp., *Tsuga* sp., *Fraxinus* sp., *Sorbus* sp., *Betula* sp., *Crataegus* sp., *Ulmus* sp., *Quercus* sp., *Fagus* sp., *Salix* sp., *Populus* sp.

Preferred trees which can be improved in accordance with the inventive method include: from the tree species *Aesculus*: *A. hippocastanum, A. pariflora, A. carnea*; from the tree species *Platanus*: *P. aceriflora, P. occidentalis, P. racemosa*; from the tree species *Picea*: *P. abies*; from the tree species *Pinus*: *P. radiate, P. ponderosa, P. contorta, P. sylvestre, P. elliottii, P. montecola, P. albicaulis, P. resinosa, P. palustris, P. taeda, P. flexilis, P. jeffregi, P. baksiana, P. strobes*; from the tree species *Eucalyptus*: *E. grandis, E. globulus, E. camadentis, E. nitens, E. obliqua, E. regnans, E. pilularus*.

Particularly preferred trees which can be improved in accordance with the inventive method include: from the tree species *Pinus*: *P. radiate, P. ponderosa, P. contorta, P. sylvestre, P. strobes*; from the tree species *Eucalyptus*: *E. grandis, E. globulus* and *E. camadentis*.

Particularly preferred trees which can be improved in accordance with the inventive method include: horse chestnut, Platanaceae, linden tree, maple tree.

The present invention can also be applied to any turf grasses, including cool-season turf grasses and warm-season turf grasses. Examples of cool-season turf grasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha* Gaudin), wood bluegrass (*Poa nemoralis* L.) and bulbous bluegrass (*Poa bulbosa* L.); bentgrasses (*Agrostis* spp.) such as creeping bentgrass (*Agrostis palustris* Huds.), colonial bentgrass (*Agrostis tenuis* Sibth.), velvet bentgrass (*Agrostis canina* L.), South German Mixed Bentgrass (*Agrostis* spp. including *Agrostis tenius* Sibth., *Agrostis canina* L., and *Agrostis palustris* Huds.), and redtop (*Agrostis alba* L.);

fescues (*Festuca* spp.), such as red fescue (*Festuca rubra* L. spp. *rubra*), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (*Festuca capillata* Lam.), tall fescue (*Festuca arundinacea* Schreb.) and meadow fescue (*Festuca elanor* L.);

ryegrasses (*Lolium* spp.), such as annual ryegrass (*Lolium multiflorum* Lam.), perennial ryegrass (*Lolium perenne* L.) and italian ryegrass (*Lolium multiflorum* Lam.);

and wheatgrasses (*Agropyron* spp.), such as fairway wheatgrass (*Agropyron cristatum* (L.) *Gaertn.*), crested wheatgrass (*Agropyron desertorum* (Fisch.) *Schult.*) and western wheatgrass (*Agropyron smithii* Rydb.).

Examples of further cool-season turfgrasses are beachgrass (*Ammophila breviligulata* Fern.), smooth bromegrass (*Bromus inermis* Leyss.), cattails such as Timothy (*Phleum pratense* L.), sand cattail (*Phleum subulatum* L.), orchardgrass (*Dactylis glomerata* L.), weeping alkaligrass (*Puccinellia distans* (L.) *Parl.*) and crested dog's-tail (*Cynosurus cristatus* L.).

Examples of warm-season turfgrasses are Bermudagrass (*Cynodon* spp. L. C. *Rich*), zoysiagrass (*Zoysia* spp. *Willd.*), St. Augustine grass (*Stenotaphrum secundatum* Walt Kuntze), centipedegrass (*Eremochloa ophiuroides* Munro Hack.), carpetgrass (*Axonopus affinis* Chase), Bahia grass (*Paspalum notatum* Flugge), Kikuyugrass (*Pennisetum clandestinum* Hochst. ex *Chiov.*), buffalo grass (*Buchloe dactyloids* (Nutt.) *Engelm.*), Blue gramma (*Bouteloua gracilis* (H.B.K.) *Lag.* ex *Griffiths*), seashore paspalum (*Paspalum vaginatum Swartz*) and sideoats grama (*Bouteloua curtipendula* (Michx. Torr.). Cool-season turfgrasses are generally preferred for the use in accordance with the invention. Especially preferred are bluegrass, bentgrass and redtop, fescues and ryegrasses. Bentgrass is especially preferred.

Particular preference is given in accordance with the invention to treating plants of the plant cultivars which are in each case commercially available or in use. Plant cultivars are understood to mean plants which have new properties ("traits") and which have been obtained by conventional breeding, by mutagenesis or with the aid of recombinant DNA techniques. Crop plants may accordingly be plants which can be obtained by conventional breeding and optimization methods or by biotechnological and genetic engineering methods or combinations of these methods, including the transgenic plants and including the plant varieties which can and cannot be protected by plant breeders' rights.

The inventive treatment method can thus also be used for the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNAi technology [RNA interference]). A heterologous gene that is located in the genome is also called a transgene. A transgene that is defined by its particular location in the plant genome is called a transformation or transgenic event.

The inventive treatment method can further be used for the treatment of genetically modified organisms (GMOs), e.g. plants or seeds in which a heterologous gene has been transiently introduced e.g. using viral vectors.

Plants and plant varieties which are preferably treated according to the invention include all plants which have genetic material which imparts particularly advantageous, useful traits to these plants (whether obtained by breeding and/or biotechnological means).

Plants and plant varieties which may also be treated according to the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can also be affected by improved plant architecture (under stress and non-stress conditions), including early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may likewise be treated according to the invention are hybrid plants that already express the characteristics of heterosis, or hybrid vigor, which results in generally higher yield, vigor, health and resistance toward biotic and abiotic stress factors. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for Brassica species (WO 1992/005251, WO 1995/009910, WO 1998/27806, WO 2005/002324, WO 2006/021972 and U.S. Pat. No. 6,229,072). However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar (e.g. WO 1991/002069).

Plants or plant varieties (obtained by plant biotechnology methods such as genetic engineering) which may also be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a petunia EPSPS (Shah et al., Science (1986), 233, 478-481), a tomato EPSPS (Gasser et al., J. Biol. Chem. (1988), 263, 4280-4289) or an Eleusine EPSPS (WO 2001/66704). It can also be a mutated EPSPS, as described, for example, in EP-A 0837944, WO 2000/066746, WO 2000/066747 or WO 2002/026995. Glyphosate-tolerant plants can also be obtained by expressing a gene that encodes a glyphosate oxidoreductase enzyme as described in U.S. Pat. Nos. 5,776,760 and 5,463,175. Glyphosate-tolerant plants can also be obtained by expressing a gene that encodes a glyphosate acetyltransferase enzyme as described, for example, in WO 2002/036782, WO 2003/092360, WO 2005/012515 and WO 2007/024782. Glyphosate-tolerant plants can also be obtained by selecting plants containing naturally occurring mutations of the above-mentioned genes as described, for example, in WO 2001/024615 or WO 2003/013226. Plants expressing EPSPS genes that confer glyphosate tolerance are described in e.g. U.S. patent application Ser. Nos. 11/517,991, 10/739,610, 12/139,408, 12/352,532, 11/312,866, 11/315,678, 12/421,292, 11/400,598, 11/651,752, 11/681,285, 11/605,824, 12/468,205, 11/760,570, 11/762,526, 11/769,327, 11/769,255, 11/943801 or 12/362,774. Plants comprising other genes that confer glyphosate tolerance, such as decarboxylase genes, are described in e.g. U.S. patent application Ser. Nos. 11/588,811, 11/185,342, 12/364,724, 11/185,560 or 12/423,926.

Other herbicide-resistant plants are for example plants which have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition e.g. described in U.S. patent application Ser. No 11/760,602. One such efficient detoxifying enzyme is, for example, an enzyme encoding a phosphinothricin acetyltransferase (such as the bar or pat protein from Streptomyces species for example). Plants expressing an exogenous phosphinothricin acetyltransferase have been described, for example, in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that have been made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD inhibitors can be transformed with a gene encoding a naturally occurring resistant HPPD enzyme such as an HPPD enzyme from non-plant organisms, such as described in WO 2011/076877, WO 2011/076882, WO2011/076892, WO 2011/076885, WO2011/076889, or HPPD enzyme from a monocot plant, such as *Avena sativa* or *Zea mays,* or having at least 98% sequence identity to an enzyme of *Avena sativa* or *Zea mays,* or an HPPD enzyme as described in WO/2011/076885, WO2011/076892, WO/2011/076877, WO/2011/076882, WO/2011/076889, or a gene encoding a mutated or chimeric HPPD enzyme according to WO 1996/038567, WO 1999/024585 and WO 1999/024586 WO 2009/144079, WO 2002/046387, WO/2011/068567, WO/2010/085705, or U.S. Pat. No. 6,768,044. Tolerance to HPPD inhibitors can also be obtained by transforming plants with genes encoding certain enzymes enabling the formation of homogentisate despite the inhibition of the native HPPD enzyme by the HPPD inhibitor. Such plants and genes are described in WO 1999/034008 and WO 2002/36787. Tolerance of plants to HPPD inhibitors can also be improved by transforming plants with a gene encoding a prephenate dehydrogenase enzyme in addition to a gene encoding an HPPD-tolerant enzyme, as described in WO 2004/024928.

Further herbicide-resistant plants are plants that have been made tolerant to acetolactate synthase (ALS) inhibitors. Known ALS inhibitors include, for example, sulfonylurea, imidazolinone, triazolopyrimidines, pyrimidinyl oxy(thio) benzoates, and/or sulfonylaminocarbonyltriazolinone herbicides. Different mutations in the ALS enzyme (also known as acetohydroxy acid synthase, AHAS) are known to confer tolerance to different herbicides and groups of herbicides, as described, for example, in Tranel and Wright, Weed Science (2002), 50, 700-712, and also in U.S. Pat. Nos. 5,605,011, 5,378,824, 5,141,870 and 5,013,659. The production of sulfonylurea-tolerant plants and imidazolinone-tolerant plants has been described in U.S. Pat. Nos. 5,605,011; 5,013,659; 5,141,870; 5,767,361; 5,731,180; 5,304,732; 4,761,373; 5,331,107; 5,928,937; and 5,378,824; and also in the international publication WO 1996/033270. Further imidazolinone-tolerant plants have also been described, for example in WO 2004/040012, WO 2004/106529, WO 2005/020673, WO 2005/093093, WO 2006/007373, WO 2006/015376, WO 2006/024351 and WO 2006/060634. Further sulfonylurea- and imidazolinone-tolerant plants have also been described, for example in WO 2007/024782, and US Patent Application No. 61/288958.

Other plants tolerant to imidazolinone and/or sulfonylurea can be obtained by induced mutagenesis, by selection in cell cultures in the presence of the herbicide or by mutation breeding, as described, for example, for soybeans in U.S. Pat. No. 5,084,082, for rice in WO 1997/41218, for sugar beet in U.S. Pat. No. 5,773,702 and WO 1999/057965, for lettuce in U.S. Pat. No. 5,198,599 or for sunflower in WO 2001/065922.

Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:

1) an insecticidal crystal protein from Bacillus thuringiensis or an insecticidal portion thereof, such as the insecticidal crystal proteins compiled by Crickmore et al., Microbiology and Molecular Biology Reviews (1998), 62, 807-813, updated by Crickmore et al. (2005) in the Bacillus thuringiensis toxin nomenclature (online at: http://www.lifesci.sussex.ac.uk/Home/Neil_Crickmore/Bt/), or insecticidal portions thereof, for example proteins of the Cry protein classes Cry1Ab, Cry1Ac, Cry1F, Cry2Ab, Cry3Ae or Cry3Bb or insecticidal portions thereof (e.g. EP 1999141 and WO2007/107302) or such proteins encoded by synthetic genes as described e.g; in U.S. patent application Ser. No. 12/249,016 or
2) a crystal protein from Bacillus thuringiensis or a portion thereof which is insecticidal in the presence of a second crystal protein other than Bacillus thuringiensis or a portion thereof, such as the binary toxin made up of the Cy34 and Cy35 crystal proteins (Moellenbeck et al., Nat. Biotechnol. (2001), 19, 668-72; Schnepf et al., Applied Environm. Microb. (2006), 71, 1765-1774); or
3) a hybrid insecticidal protein comprising parts of two different insecticidal crystal proteins from Bacillus thuringiensis, such as a hybrid of the proteins of 1) above or a hybrid of the proteins of 2) above, for example the Cry1A.105 protein produced by corn event MON98034 (WO 2007/027777); or
4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in corn events MON863 or MON88017, or the Cry3A protein in corn event MIR604; or
5) an insecticidal secreted protein from Bacillus thuringiensis or Bacillus cereus, or an insecticidal portion thereof, such as the vegetative insecticidal proteins (VIPs) listed under the following link, for example proteins from the VIP3Aa protein class: http://www.lifesci.sussex.ac.uk/Home/Neil_Crickmore/Bt/vip.html or
6) a secreted protein from Bacillus thuringiensis or Bacillus cereus which is insecticidal in the presence of a second secreted protein from Bacillus thuringiensis or B. cereus, such as the binary toxin made up of the VIP1A and VIP2A proteins (WO 1994/21795); or
7) a hybrid insecticidal protein comprising parts from different secreted proteins from Bacillus thuringiensis or Bacillus cereus, such as a hybrid of the proteins in 1) above or a hybrid of the proteins in 2) above; or
8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Examples of nematode resistant plants are described in e.g. U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396 or 12/497,221.

Plants or plant varieties (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:

a. plants which contain a transgene capable of reducing the expression and/or the activity of the poly(ADP-ribose) polymerase (PARP) gene in the plant cells or plants, as described in WO 2000/004173 or EP 04077984.5 or EP 06009836.5;

b. plants which contain a stress tolerance-enhancing transgene capable of reducing the expression and/or the activity of the PARG encoding genes of the plants or plant cells, as described, for example, in WO 2004/090140;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase, as described, for example, in EP 04077624.7 or WO 2006/133827 or PCT/EP07/002433.

Plants or plant varieties (obtained by plant biotechnology methods such as genetic engineering) which may also be treated according to the invention show altered quantity, quality and/or storage stability of the harvested product and/or altered properties of specific ingredients of the harvested product such as, for example:

1) Transgenic plants which synthesize a modified starch which is altered with respect to its chemophysical traits, in particular the amylose content or the amylose/amylopectin ratio, the degree of branching, the average chain length, the distribution of the side chains, the viscosity behavior, the gel resistance, the grain size and/or grain morphology of the starch in comparison to the synthesized starch in wild-type plant cells or plants, such that this modified starch is better suited for certain applications. These transgenic plants synthesizing a modified starch are described, for example, in EP 0571427, WO 1995/004826, EP 0719338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, WO 99/58688, WO 1999/58690, WO 1999/58654, WO 2000/008184, WO 2000/008185, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192, WO 1998/22604, WO 1998/32326, WO 2001/98509, WO 2001/98509, WO 2005/002359, U.S. Pat. Nos. 5,824,790, 6,013,861, WO 1994/004693, WO 1994/009144, WO 1994/11520, WO 1995/35026 and WO 1997/20936.

2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, as described in EP 0663956, WO 1996/001904, WO 1996/021023, WO 1998/039460 and WO 1999/024593, plants which produce alpha-1,4-glucans, as described in WO 1995/031553, US 2002/031826, U.S. Pat. Nos. 6,284,479, 5,712,107, WO 1997/047806, WO 1997/047807, WO 1997/047808 and WO 2000/14249, plants which produce alpha-1,6-branched alpha-1,4-glucans, as described in WO 2000/73422, and plants which produce alternan, as described in WO 2000/047727, EP 06077301.7, U.S. Pat. No. 5,908,975 and EP 0728213.

3) Transgenic plants which produce hyaluronan, as described, for example, in WO 2006/032538, WO 2007/039314, WO 2007/039315, WO 2007/039316, JP 2006/304779 and WO 2005/012529.

4) 4) transgenic plants or hybrid plants, such as onions with characteristics such as 'high soluble solids content', 'low pungency' (LP) and/or 'long storage' (LS), as described in U.S. patent application Ser. Nos. 12/020,360 and 61/054,026

Plants or plant varieties (obtained by plant biotechnology methods such as genetic engineering) which may also be treated according to the invention are plants, such as cotton plants, with altered fiber characteristics. Such plants can be obtained by genetic transformation, or by selection of plants containing a mutation imparting such altered fiber characteristics and include:

a) plants, such as cotton plants, which contain an altered form of cellulose synthase genes, as described in WO 1998/000549;

b) plants, such as cotton plants, which contain an altered form of rsw2 or rsw3 homologous nucleic acids, as described in WO 2004/053219;

c) plants, such as cotton plants, with an increased expression of sucrose phosphate synthase, as described in WO 2001/017333;

d) plants, such as cotton plants, with an increased expression of sucrose synthase, as described in WO 02/45485;

e) plants, such as cotton plants, wherein the timing of the plasmodesmatal gating at the basis of the fiber cell is altered, for example through downregulation of fiber-selective β-1,3-glucanase, as described in WO 2005/017157;

f) plants, such as cotton plants, which have fibers with altered reactivity, for example through the expression of the N-acetylglucosaminetransferase gene including nodC and chitin synthase genes, as described in WO 2006/136351.

Plants or plant cultivars (obtained by plant biotechnology methods such as genetic engineering) which may also be treated according to the invention are plants, such as oilseed rape or related Brassica plants, with altered oil profile characteristics. Such plants can be obtained by genetic transformation or by selection of plants containing a mutation imparting such altered oil characteristics and include:

a) plants, such as oilseed rape plants, which produce oil having a high oleic acid content, as described, for example, in U.S. Pat. Nos. 5,969,169, 5,840,946 or 6,323,392 or 6,063,947;

b) plants, such as oilseed rape plants, which produce oil having a low linolenic acid content, as described in U.S. Pat. Nos. 6,270,828, 6,169,190 or 5,965,755;

c) plants, such as oilseed rape plants, which produce oil having a low level of saturated fatty acids, as described, for example, in U.S. Pat. No. 5,434,283 or U.S. patent application Ser. No. 12/668,303

Plants or plant cultivars (that can be obtained by plant biotechnology methods such as genetic engineering) which may also be treated according to the invention are plants, such as oilseed rape or related Brassica plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. Patent Appl. No. 61/135,230, WO09/068313 and WO10/006732.

Particularly useful transgenic plants which may be treated according to the invention are plants which comprise one or more genes which encode one or more toxins and are the transgenic plants available under the following trade names: YIELD GARD® (for example corn, cotton, soybeans), KnockOut® (for example corn), BiteGard® (for example corn), BT-Xtra® (for example corn), Bollgard® (cotton), Nucotn® (cotton), Nucotn 33B® (cotton), NatureGard® (for example corn), Protecta®, Agrisure® (corn), Herculex® (corn), MaizeGard® (corn), MaxGard™(corn), Twin-Link® (cotton), VIPCot® (cotton), Widestrike™ (cotton) and NewLeaf® (potato). Examples of herbicide-tolerant plants which may be mentioned are corn varieties, cotton varieties and soybean varieties which are available under the following trade names: Roundup Ready® (tolerance to glyphosate, for example corn, cotton, soybeans), Glytol® (tolerance to glyphosate, cotton) Liberty Link® (tolerance to phosphinothricin, for example oilseed rape, cotton, soybean), IMI® (tolerance to imidazolinone), Optimum™ Gat™ (tolerance to sulfonylurea and glyphosate) and SCS® (tolerance to sulfonylurea, for example corn) and Enlist™ (tolerance to 2,4-D and glyphosate). Herbicide-resistant plants (plants bred in a conventional manner for herbicide tolerance) which may be mentioned include the varieties sold under the name Clearfield® (for example corn). Further transgenic plant varieties having improved characteristics are sold under trade names including InVigor® (canola), Amflora® (potatoes) Mavera® (corn). Varieties combining different events may be sold under tradenames including SmartStax®.

Particularly useful transgenic plants which may be treated according to the invention are plants containing transformation events, or a combination of transformation events, and that are listed for example in the databases for various national or regional regulatory agencies including Event 1143-14A (cotton, insect control, not deposited, described in WO2006/128569); Event 1143-51 B (cotton, insect control, not deposited, described in WO2006/128570); Event 1445 (cotton, herbicide tolerance, not deposited, described in US2002120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control—herbicide tolerance, deposited as PTA-6233, described in WO2005/103266 or US2005216969); Event 3006-210-23 (cotton, insect control—herbicide tolerance, deposited as PTA-6233, described in US2007143876 or WO2005/103266); Event 3272 (corn, quality trait, deposited as PTA-9972, described in WO2006098952 or US2006230473); Event 40416 (corn, insect control—herbicide tolerance, deposited as ATCC PTA-11508, described in WO2011/075593); Event 43A47 (corn, insect control—herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US2006162007 or WO2004053062); Event B16 (corn, herbicide tolerance, not deposited, described in US2003126634); Event BPS-CV127-9 (soybean, herbicide tolerance, deposited as NCIMB No. 41603, described in WO2010/080829); Event CE43-67B (cotton, insect control, deposited as DSM ACC2724, described in US2009217423 or WO2006/128573); Event CE44-69D (cotton, insect control, not deposited, described in US20100024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US2006130175 or WO2004039986); Event COT202 (cotton, insect control, not deposited, described in US2007067868 or WO2005054479); Event COT203 (cotton, insect control, not deposited, described in WO2005/054480); Event DAS40278 (corn, herbicide tolerance, deposited as ATCC PTA-10244, described in WO2011/022469); Event DAS-59122-7 (corn, insect control—herbicide tolerance, deposited as ATCC PTA 11384, described in US2006070139); Event DAS-59132 (corn, insect control—herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US2009137395 or WO2008/112019); Event DP-305423-1 (soybean, quality trait, not deposited, described in US2008312082 or WO2008/054747); Event DP-32138-1 (corn, hybridization system, deposited as ATCC PTA-9158, described in US20090210970 or WO2009/103049); Event DP-356043-5 (soybean, herbicide tolerance, deposited as ATCC PTA-8287, described in US20100184079 or WO2008/002872); Event EE-1 (brinjal, insect control, not deposited, described in WO2007/091277); Event Fl117 (corn, herbicide tolerance, deposited as ATCC 209031, described in US2006059581 or WO1998/044140); Event GA21 (corn, herbicide tolerance, deposited as ATCC 209033, described in US2005086719 or WO1998/044140); Event GG25 (corn, herbicide tolerance, deposited as ATCC 209032, described in US2005188434 or WO1998/044140); Event GHB119 (cotton, insect control—herbicide tolerance, deposited as ATCC PTA-8398, described in WO2008/151780); Event GHB614 (cotton, herbicide tolerance, deposited as ATCC PTA-6878, described in US2010050282 or WO2007/017186); Event GJ11 (corn, herbicide tolerance, deposited as ATCC 209030, described in US2005188434 or WO1998/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US2004172669 or WO2004/074492); Event JOPLIN1 (wheat, disease tolerance, not deposited, described in US2008064032); Event LL27 (soybean, herbicide tolerance, deposited as NCIMB41658, described in WO2006/108674 or US2008320616); Event LL55 (soybean, herbicide tolerance, deposited as NCIMB 41660, described in WO2006/108675 or US2008196127); Event LLcotton25 (cotton, herbicide tolerance, deposited as ATCC PTA-3343, described in WO2003013224 or US2003097687); Event LLRICE06 (rice, herbicide tolerance, deposited as ATCC-23352, described in U.S. Pat. No. 6,468,747 or WO2000/026345); Event LLRICE601 (rice, herbicide tolerance, deposited as ATCC PTA-2600, described in US20082289060 or WO2000/026356); Event LY038 (corn, quality trait, deposited as ATCC PTA-5623, described in US2007028322 or WO2005061720); Event MIR162 (corn, insect control, deposited as PTA-8166, described in US2009300784 or WO2007/142840); Event MIR604 (corn, insect control, not deposited, described in US2008167456 or WO2005103301); Event MON15985 (cotton, insect control, deposited as ATCC PTA-2516, described in US2004-250317 or WO2002/100163); Event MON810 (corn, insect control, not deposited, described in US2002102582); Event MON863 (corn, insect control, deposited as ATCC PTA-2605, described in WO2004/011601 or US2006095986); Event MON87427 (corn, pollination control, deposited as ATCC PTA-7899, described in WO2011/062904); Event MON87460 (corn, stress tolerance, deposited as ATCC PTA-8910, described in WO2009/111263 or US20110138504); Event MON87701 (soybean, insect control, deposited as ATCC PTA-8194, described in US2009130071 or WO2009/064652); Event MON87705 (soybean, quality trait—herbicide tolerance, deposited as ATCC PTA-9241, described in US20100080887 or WO2010/037016); Event MON87708 (soybean, herbicide tolerance, deposited as ATCC PTA9670, described in WO2011/034704); Event MON87754 (soybean, quality trait, deposited as ATCC PTA-9385, described in WO2010/024976); Event MON87769 (soybean, quality trait, deposited as ATCC PTA-8911, described in US20110067141 or WO2009/102873); Event MON88017 (corn, insect control—herbicide tolerance, deposited as ATCC PTA-5582, described in US2008028482 or WO2005/059103); Event MON88913 (cotton, herbicide tolerance, deposited as ATCC PTA-4854, described in WO2004/072235 or US2006059590); Event MON89034 (corn, insect control, deposited as ATCC PTA-7455, described in WO2007/140256 or US2008260932); Event MON89788 (soybean, herbicide tolerance, deposited as ATCC PTA-6708, described in US2006282915 or WO2006/130436); Event MS11 (oilseed rape, pollination control—herbicide tolerance, deposited as ATCC PTA-850 or PTA-2485, described in WO2001/031042); Event MS8 (oilseed rape, pollination control—herbicide tolerance, deposited as ATCC PTA-730, described in WO2001/041558 or US2003188347); Event NK603 (corn, herbicide tolerance, deposited as ATCC PTA-2478, described in US2007-292854); Event PE-7 (rice, insect control, not deposited, described in WO2008/114282); Event RF3 (oilseed rape, pollination control—herbicide tolerance, deposited as ATCC PTA-730, described in WO2001/041558 or US2003188347); Event RT73 (oilseed rape, herbicide tolerance, not deposited, described in WO2002/036831 or US2008070260); Event T227-1 (sugar beet, herbicide tolerance, not deposited, described in WO2002/44407 or US2009265817); Event T25 (corn, herbicide tolerance, not deposited, described in US2001029014 or WO2001/051654); Event T304-40 (cotton, insect control—herbicide tolerance, deposited as ATCC PTA-8171, described in US2010077501 or WO2008/122406); Event T342-142 (cotton, insect control, not deposited, described in WO2006/128568); Event TC1507 (corn, insect control—herbicide tolerance, not deposited, described in US2005039226 or WO2004/099447); Event VIP1034 (corn, insect control—herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621).

The Compounds (A), preferably Compound (A1) to be used in accordance with the invention, either alone or in combination with other agrochemical compounds, especially with those that are above defined as the preferred ones from the group consisting of funigicides, insecticides, and plant growth regulators, can be converted to customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active ingredient, synthetic substances impregnated with active ingredient, fertilizers, and also microencapsulations in polymeric substances. In the context of the present invention, it is especially preferred when Compounds (A), preferably Compound (A1) are/is used in accordance with the invention, either alone or in combination with other agrochemical compounds, especially with those that are above defined as the preferred ones from the group consisting of funigicides, insecticides, and plant growth regulatorsare used in the form of a spray formulation.

The present invention therefore also relates to a spray formulation for increasing the yield of useful plants or crop plants with respect to their harvested plant organs. A spray formulation is described in detail hereinafter:

The formulations for spray application are produced in a known manner, for example by mixing Compounds (A), preferably Compound (A1) to be used in accordance with the invention, either alone or in combination with other agrochemical compounds, especially with those that are above defined as the preferred ones from the group consisting of funigicides, insecticides, and plant growth regulators-invention with extenders, i.e. liquid solvents and/or solid carriers, optionally with use of surfactants, i.e. emulsifiers and/or dispersants and/or foam formers. Further customary additives, for example customary extenders and solvents or diluents, dyes, wetting agents, dispersants, emulsifiers, antifoams, preservatives, secondary thickeners, stickers, gibberellins and also water, can optionally also be used. The formulations are prepared either in suitable equipment or else before or during application.

The auxiliaries used may be those substances which are suitable for imparting, to the composition itself and/or to preparations derived therefrom (for example spray liquors), particular properties such as particular technical properties and/or else special biological properties. Useful typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender used is water, it is also possible to use, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulfoxide, and also water.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Useful wetting agents which may be present in the formulations usable in accordance with the invention are all substances which promote wetting and which are conventionally used for the formulation of active agrochemical ingredients. Preference is given to using alkyl naphthalenesulfonates, such as diisopropyl or diisobutyl naphthalenesulfonates.

Useful dispersants and/or emulsifiers which may be present in the formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Suitable nonionic dispersants are especially ethylene oxide/propylene oxide block polymers, alkylphenol polyglycol ethers and tristryrylphenol polyglycol ether, and the phosphated or sulfated derivatives thereof. Suitable anionic dispersants are especially lignosulfonates, salts of polyacrylic acid and arylsulfonate/formaldehyde condensates.

Antifoams which may be present in the formulations usable in accordance with the invention are all foam-inhibiting substances conventionally used for the formulation of active agrochemical ingredients. Usable with preference are silicone antifoams and magnesium stearate.

Preservatives which may be present in the formulations usable in accordance with the invention are all substances usable for such purposes in agrochemical compositions. Examples include dichlorophene and benzyl alcohol hemiformal.

Secondary thickeners which may be present in the formulations usable in accordance with the invention are all substances usable for such purposes in agrochemical compositions. Preference is given to cellulose derivatives, acrylic acid derivatives, xanthan, modified clays and finely divided silica.

Stickers which may be present in the formulations usable in accordance with the invention include all customary binders usable in seed-dressing products. Preferred examples include polyvinylpyrrolidone, polyvinyl acetate, polyvinyl alcohol and tylose. Gibberellins which may be present in the formulations usable in accordance with the invention may preferably be gibberellins A1, A3 (=gibberellic acid), A4 and A7; particular preference is given to using gibberellic acid. The gibberellins are known (cf. R. Wegler "Chemie der Pflanzenschutz- and Schadlingsbekampfungsmittel" [Chemistry of Crop Protection Compositions and Pesticides], vol. 2, Springer Verlag, 1970, p. 401-412).

Further additives may be fragrances, mineral or vegetable, optionally modified oils, waxes and nutrients (including trace nutrients), such as salts of iron, manganese, boron, copper, cobalt, molybdenum and zinc. Additionally present may be stabilizers, such as cold stabilizers, antioxidants, light stabilizers or other agents which improve chemical and/or physical stability.

The formulations contain generally between 0.01 and 98% by weight, preferably between 0.5 and 90%, of the compound of the formula (I).

In wettable powders, the active ingredient concentration is, for example, from about 10 to 90% by weight; the remainder to 100% by weight consists of customary formulation constituents. In the case of emulsifiable concentrates, the active ingredient concentration may be from about 1 to 90% by weight, preferably from 5 to 80% by weight. Dust-type formulations contain from 1 to 30% by weight of active ingredient, preferably usually from 5 to 20% by weight of active ingredient; sprayable solutions contain from about 0.05 to 80% by weight, preferably from 2 to 50% by weight of active ingredient. In water-dispersible granules, the active ingredient content depends partly on whether the active compound is present in solid or liquid form and which granulation assistants, fillers, etc. are used. In the granules dispersible in water, the content of active ingredient is, for example, between 1 and 95% by weight, preferably between 10 and 80% by weight.

The active ingredient when used according to present invention may be present in its commercially available formulations and in the use forms, prepared from these formulations, in a mixture with other active ingredients, such as insecticides, attractants, sterilants, bactericides, acaricides, nematicides, fungicides, growth regulators, herbicides, safeners, fertilizers or semiochemicals.

Preferred times for the application of compounds of the formula (I) for regulating plant growth are treatments of the soil, stems and/or leaves with the approved application rates.

Compounds(A), preferably Compound (A1), when used according to present invention, either solely or in combination with one or more above mentioned preferred agrochemical compounds, may generally additionally be present in their commercial formulations and in the use forms prepared from these formulations in mixtures with other active ingredients, such as insecticides, attractants, sterilants, acaricides, nematicides, fungicides, growth regulators, substances which influence plant maturity, safeners or herbicides. Particularly further suitable mixing partners are, for example, the active ingredients of the different classes, specified below in groups, without any preference resulting from the sequence thereof:

Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulfate and other copper preparations.

Insecticides/acaricides/nematicides:
I1) acetylcholine esterase (AChE) inhibitors, a) from the substance group of the carbamates, for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, fenoxycarb, formetanate, furathiocarb, isoprocarb, metam-sodium, methio¬carb, metho¬myl, metolcarb, oxamyl, pirimicarb, pro¬mecarb, propoxur, thiofanox, trimethacarb, XMC, xylylcarb, triazamate, b) from the group of the organophosphates, for example acephate, azamethiphos, azinphos (-methyl, ethyl), bromophos-ethyl, bromfenvinfos (-methyl), butathiofos, cadusafos, carbophenothion, chlorethoxyfos, chlorfenvinphos, chlormephos, coumaphos, cyanofenphos, cyanophos, chlorfenvinphos, demeton-S-methyl, demeton-S-methylsulfone, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion I2) sodium channel modulators/voltage-dependent sodium channel blockers, a) from the group of the pyrethroids, for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, eflusilanate, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, pyrethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum), b) DDT, c) oxadiazines, for example indoxacarb, d) semicarbazones, for example metaflumizone (BAS3201)

I3) acetylcholine receptor agonists/antagonists, a) from the group of the chloronicotinyls, for example acetamiprid, AKD 1022, dinotefuran, imidaclothiz, nitenpyram, nithiazine, thiacloprid, b) nicotine, bensultap, cartap;

I4) acetylcholine receptor modulators from the group of the spinosyns,

I5) GABA-controlled chloride channel antagonists, a) from the group of the organochlorines, for example camphechlor, chlordane, endosulfan, gamma-HCH, HCH, heptachlor, lindane, methoxychlor, b) fiproles, for example acetoprole, pyrafluprole, pyriprole, vaniliprole;

I6) chloride channel activators, for example emamectin, ivermectin, lepimectin, milbemycin;

I7) juvenile hormone mimetics, for example diofenolan, epofenonane, fenoxycarb, hydroprene, kinoprene, methoprene, pyriproxifen, triprene;

I8) ecdysone agonists/disruptors, for example chromafenozide, halofenozide, methoxyfenozide, tebufenozide;

I9) chitin biosynthesis inhibitors, for example bistrifluron, chlofluazuron, diflubenzuron, fluazuron, flucycloxuron, flufenoxuron, hexaflumuron, novaluron, noviflumuron, penfluron, teflubenzuron, buprofezin, cyromazine;

I10) inhibitors of oxidative phosphorylation, a) ATP disruptors, for example diafenthiuron, b) organotin compounds, for example azocyclotin, cyhexatin, fenbutatin oxide;

I11) decouplers of oxidative phosphorylation by interruption of the H-proton gradient, a) from the group of the pyrroles, for example chlorofenapyr, b) from the class of the dinitrophenols, for example binapacyrl, dinobuton, dinocap, DNOC, meptyldinocap;

I12) site I electron transport inhibitors, for example METIs, especially, as examples, fenazaquin, fenpyroximate, pyrimidifen, pyridaben, tebufenpyrad, tolfenpyrad or else hydramethylnon, dicofol I13) site II electron transport inhibitors, for example rotenone I14) site III electron transport inhibitors, for example acequinocyl, fluacrypyrim I15) microbial disruptors of the insect gut membrane, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins, for example Cry1Ab, Cry1Ac, Cry1Fa, Cry2Ab, mCry3A, Cry3Ab, Cry3Bb, Cry34/35Ab1

I16) lipid synthesis inhibitors, a) from the group of the tetronic acids, for example spirodiclofen, spiromesifen, b) from the class of the tetramic acids, for example spirotetramat, cis-3-(2,5-dimethylphenyl)-4-hydroxy-8-methoxy-1-azaspiro[4.5]dec-3-en-2-one I17) octopaminergic agonists, for example amitraz I18) inhibitors of magnesium-stimulated ATPase, for example propargite I19) nereistoxin analogs, for example thiocyclam hydrogen oxalate, thiosultap-sodium I20) ryanodine receptor agonists, a) from the group of the benzenedicarboxamides, b) from the group of the anthranilamides, 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) or methyl 2-[3,5-dibromo-2-({[3-bromo-1-(3-chloropyridin-2-yl)-1H-pyrazol-5-yl]carbonyl}amino)benzoyl]-1,2-dimethylhydrazinecarboxylate (known from WO2007/043677)

I21) biologics, hormones or pheromones, for example azadirachtin, *Bacillus* spec., *Beauveria* spec., codlemone, *Metarrhizium* spec., *Paecilomyces* spec., thuringiensin, *Verticillium* spec.

I22) active ingredients with unknown or nonspecific mechanisms of action, a) fumigants, for example aluminum phosphide, methyl bromide, sulfuryl fluoride, b) antifeedants, for example cryolite, flonicamide, pymetrozine, c) mite growth inhibitors, for example clofentezine, etoxazole, hexythiazox, d) amidoflumet, benclothiaz, benzoximate, bifenazate, bromopropylate, buprofezin, chinomethionat, chlorodimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin and the following known active compounds: 4-{[(6-bromopyrid-3-yl)methyl](2-fluoroethyl)amino}furan-2(5H)-one (known from WO 2007/115644), 4-{[(6-fluoropyrid-3-yl)methyl](2,2-difluoroethyl)amino}furan-2(5H)-one (known from WO 2007/115644), 4-{[(2-chloro-1,3-thiazol-5-yl)methyl](2-fluoroethyl)amino}furan-2(5H)-one (known from WO 2007/115644), 4-{[(6-chloropyrid-3-yl)methyl](2-fluoroethyl)amino}furan-2(5H)-one (known from WO 2007/115644), 4-{[(6-chloropyrid-3-yl)methyl](2,2-difluoroethyl)amino}furan-2(5H)-one (known from WO 2007/115644), 4-{[(6-chloro-5-fluoropyrid-3-yl)methyl](methyl)amino}furan-2(5H)-one (known from WO 2007/115643), 4-{[(5,6-dichloropyrid-3-yl)methyl](2-fluoroethyl)amino}furan-2(5H)-one (known from WO 2007/115646), 4-{[(6-chloro-5-fluoropyrid-3-yl)methyl](cyclopropyl)amino}furan-2(5H)-one (known from WO 2007/115643), 4-{[(6-chloropyrid-3-yl)methyl](cyclopropyl)amino}furan-2(5H)-one (known from EP0539588), 4-{[(6-chloropyrid-3-yl)methyl](methyl)amino}furan-2(5H)-one (known from EP0539588), [1-(6-chloropyridin-3-yl)ethyl](methyhoxido-λ4-sulfanylidenecyanamide (known from WO 2007/149134) and the diastereomers thereof {[(R1R)-1-(6-chloropyridin-3- yl)ethyl](methyl)oxido-lambda6-sulfanylidene}cyanamide and {[(1S)-1-(6-chloropyridin-3-yl)ethyl](methyhoxido-lambda6-sulfanylidene}cyanamide (likewise known from WO 2007/149134) and 1-[2-fluoro-4-methyl-5-[(2,2,2-trifluoroethyl)sulfinyl]phenyl]-3-(trifluoromethyl)-1H-1,2,4-triazol-5-amine (known from WO 2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropane-carboxylate (known from WO 2006/129714), 2-cyano-3-(difluoromethoxy)-N,N-dimethylbenzenesulfonamide (known from WO2006/056433), 2-cyano-3-(difluoromethoxy)-N-methylbenzenesulfonamide (known from WO2006/100288), 2-cyano-3-(difluoromethoxy)-N-ethylbenzenesulfonamide (known from WO2005/035486), 4-(difluoromethoxy)-N-ethyl-N-methyl-1,2-benzothiazole-3-amine 1,1-dioxide (known from WO2007/057407), N-[1-(2,3-dimethylphenyl)-2-(3,5-dimethylphenyl)ethyl]-4,5-dihydro-1,3-thiazole-2-amine (known from WO2008/104503), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003106457), 3-(2,5-dimethylphenyl)-4-hydroxy-8-methoxy-1,8-diazaspiro[4.5]dec-3-en-2-one (known from WO2009049851), 3-(2,5-dimethylphenyl)-8-methoxy-2-oxo-1,8-diazaspiro[4.5]dec-3-en-4-yl ethyl carbonate (known from WO2009049851), 4-(but-2-yn-1-yloxy)-6-(3,5-dimethylpiperidin-1-yl)-5-fluoropyrimidine (known from WO2004099160), (2,2,3,3,4,4,5,5-octafluoropentyl)(3,3,3-trifluoropropyl)malononitrile (known from WO2005063094), (2,2,3,3,4,4,5,5-octafluoropentyl)(3,3,4,4,4-pentafluorobutyl)malononitrile (known from WO2005063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO2007040280/282), 2-ethyl-7-methoxy-3-methyl-6-[(2,2,3,3-tetrafluoro-2,3-dihydro-1,4-benzodioxin-6-yl)oxy]quinolin-4-yl methyl carbonate (known from JP2008110953), 2-ethyl-7-methoxy-3-methyl-6-[(2,2,3,3-tetrafluoro-2,3-dihydro-1,4-benzodioxin-6-yl)oxy]quinolin-4-yl acetate (known from JP2008110953), PF1364 (Chemical Abstracts No. 1204776-60-2, known from JP2010018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005085216).

Safeners are preferably selected from the group consisting of:
S1) compounds of the formula (S1

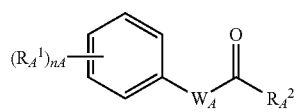

(S1)

where the symbols and indices are each defined as follows:
$n_A$ is a natural number from 0 to 5, preferably 0 to 3;
$R_A^1$ is halogen, $(C_1-C_4)$-alkyl, $(C_1-C_4)$-alkoxy, nitro or $(C_1-C_4)$-haloalkyl;

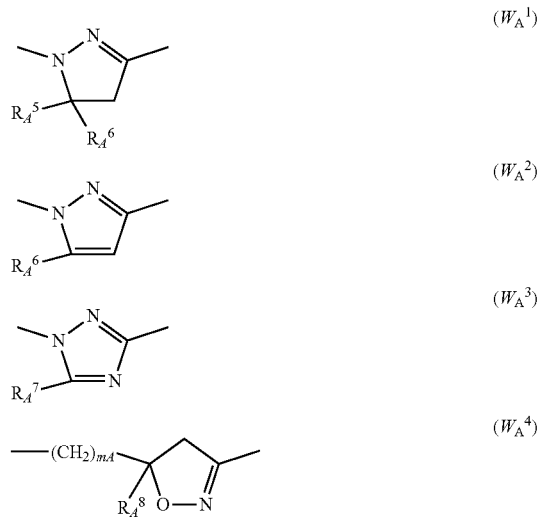

$W_A$ is an unsubstituted or substituted divalent heterocyclic radical from the group consisting of partially unsaturated or aromatic five-membered heterocycles having 1 to 3 hetero ring atoms from the group of N and O, where at least one nitrogen atom and at most one oxygen atom is present in the ring, preferably a radical from the group consisting of $(W_A^1)$ to $(W_A^4)$,
$m_A$ is 0 or 1;
$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group consisting of O and S, which is attached via the nitrogen atom to the carbonyl group in (S1) and which is unsubstituted or substituted by radicals from the group consisting of $(C_1-C_4)$-alkyl, $(C_1-C_4)$-alkoxy and optionally substituted phenyl, preferably a radical of the formula $OR_A^3$, $NHR_A^4$ or $N(CH_3)_2$, in particular of the formula $OR_A^3$;
$R_A^3$ is hydrogen or an unsubstituted or substituted aliphatic hydrocarbyl radical, preferably having a total of 1 to 18 carbon atoms;
$R_A^4$ is hydrogen, $(C_1-C_6)$-alkyl, $(C_1-C_6)$-alkoxy or substituted or unsubstituted phenyl;
$R_A^5$ is H, $(C_1-C_8)$-alkyl, $(C_1-C_8)$-haloalkyl, $(C_1-C_4)$-alkoxy-$(C_1-C_8)$-alkyl, cyano or $COOR_A^9$ where $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;
$R_A^6$, $R_A^7$, $R_A^8$ are the same or different and are each hydrogen, $(C_1-C_8)$-alkyl, $(C_1-C_8)$-haloalkyl, $(C_3-C_{12})$-cycloalkyl or substituted or unsubstituted phenyl;
preferably:
a) compounds of the type of the dichlorophenylpyrazoline-3-carboxylic acid (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds, as described in WO-A-91/07874;
b) derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds, as described in EP-A-333 131 and EP-A-269 806;
c) derivatives of 1,5-diphenylpyrazole-3-carboxylic acid (S1$^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds, as described, for example, in EP-A-268554;
d) compounds of the triazolecarboxylic acid type (S1$^d$), preferably compounds such as fenchlorazole(-ethyl), i.e. ethyl 1-(2,4-dichlorophenyl)-5-trichloromethyl-(1H)-1,2,4-triazole-3-carboxylate (S1-7), and related compounds as described in EP-A-174 562 and EP-A-346 620;
e) compounds of the 5-benzyl- or 5-phenyl-2-isoxazoline-3-carboxylic acid or of the 5,5-diphenyl-2-isoxazoline-3-carboxylic acid type (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazolinecarboxylic acid (S1-10) or ethyl 5,5-diphenyl-2-isoxazoline-3-carboxylate (S1-11) ("isoxadifen-ethyl") or n-propyl 5,5-diphenyl-2-isoxazoline-3-carboxylate (S1-12) or ethyl 5-(4-fluorophenyl)-5-phenyl-2-isoxazoline-3-carboxylate (S1-13), as described in patent application WO-A-95/07897.

S2) Quinoline derivatives of the formula (S2),

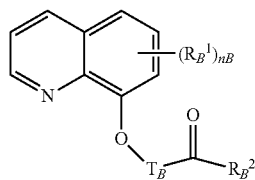

(S2)

where the symbols and indices are each defined as follows:
$R_B^1$ is halogen, $(C_1\text{-}C_4)$-alkyl, $(C_1\text{-}C_4)$-alkoxy, nitro or $(C_1\text{-}C_4)$-haloalkyl;
$n_B$ is a natural number from 0 to 5, preferably 0 to 3;
$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, preferably from the group consisting of O and S, which is attached via the nitrogen atom to the carbonyl group in (S2) and which is unsubstituted or substituted by radicals from the group consisting of $(C_1\text{-}C_4)$-alkyl, $(C_1\text{-}C_4)$-alkoxy and optionally substituted phenyl, preferably a radical of the formula $OR_B^3$, $NHR_B^4$ or $N(CH_3)_2$, in particular of the formula $OR_B^3$;
$R_B^3$ is hydrogen or an unsubstituted or substituted aliphatic hydrocarbyl radical, preferably having a total of 1 to 18 carbon atoms;
$R_B^4$ is hydrogen, $(C_1\text{-}C_6)$-alkyl, $(C_1\text{-}C_6)$-alkoxy or substituted or unsubstituted phenyl;
$T_B$ is a $(C_1\text{-}$ or $C_2)$-alkanediyl chain which is unsubstituted or substituted by one or two $(C_1\text{-}C_4)$-alkyl radicals or by $[(C_1\text{-}C_3)\text{-alkoxy}]$carbonyl;
preferably:
a) compounds of the 8-quinolinoxyacetic acid type (S2$^a$), preferably 1-methylhexyl (5-chloro-8-quinolinoxy)acetate ("cloquintocet-mexyl") (S2-1), 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxoprop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), hydrates and salts thereof, for example the lithium, sodium, potassium, calcium, magnesium, aluminum, iron, ammonium, quaternary ammonium, sulfonium or phosphonium salts thereof, as described in WO-A-2002/34048;
b) compounds of the (5-chloro-8-quinolinoxy)malonic acid type (S2$^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds as described in EP-A-0 582 198.

S3) Compounds of the formula (S3)

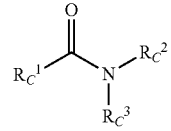

(S3)

where the symbols and indices are each defined as follows:
$R_C^1$ is $(C_1\text{-}C_4)$-alkyl, $(C_1\text{-}C_4)$-haloalkyl, $(C_2\text{-}C_4)$-alkenyl, $(C_2\text{-}C_4)$-haloalkenyl, $(C_3\text{-}C_7)$-cycloalkyl, preferably dichloromethyl;
$R_C^2$, $R_C^3$ are the same or different and are each hydrogen, $(C_1\text{-}C_4)$-alkyl, $(C_2\text{-}C_4)$-alkenyl, $(C_2\text{-}C_4)$-alkynyl, $(C_1\text{-}C_4)$-haloalkyl, $(C_2\text{-}C_4)$-haloalkenyl, $(C_1\text{-}C_4)$-alkylcarbamoyl-$(C_1\text{-}C_4)$-alkyl, $(C_2\text{-}C_4)$-alkenylcarbamoyl-$(C_1\text{-}C_4)$-alkyl, $(C_1\text{-}C_4)$-alkoxy-$(C_1\text{-}C_4)$-alkyl, dioxolanyl-$(C_1\text{-}C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring; preferably: active ingredients of the dichloroacetamide type, which are frequently used as pre-emergence safeners (soil-acting safeners), for example "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N-[(allylaminocarbonyl)methyl]dichloroacetamide) from Sagro-Chem (S3-6), "AD-67" or "MON 4660" (3-dichloroacetyl-1-oxa-3-azaspiro[4,5]decane) from Nitrokemia or Monsanto (S3-7), "TI-35" (1-dichloroacetylazepane) from TRI-Chemical RT (S3-8), "diclonon" (dicyclonone) or "BAS145138" or "LAB145138" (S3-9) ((RS)-1-dichloroacetyl-3,3,8a-trimethylperhydropyrrolo[1,2-a]pyrimidin-6-one) from BASF, "furilazole" or "MON 13900" ((RS)-3-dichloroacetyl-5-(2-furyl)-2,2-dimethyloxazolidine) (S3-10); and the (R) isomer thereof (S3-11).

S4) N-Acylsulfonamides of the formula (S4) and salts thereof, of the formula (S4a) below, which are known, for example, from WO-A-97/45016

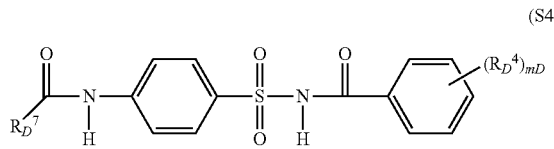
(S4a)

in which
R$_D^7$ is (C$_1$-C$_6$)-alkyl, (C$_3$-C$_6$)-cycloalkyl, where the 2 latter radicals are substituted by v$_D$ substituents from the group consisting of halogen, (C$_1$-C$_4$)-alkoxy, (C$_1$-C$_6$)-haloalkoxy and (C$_1$-C$_4$)-alkylthio and, in the case of cyclic radicals, also (C$_1$-C$_4$)-alkyl and (C$_1$-C$_4$)-haloalkyl;
R$_D^4$ is halogen, (C$_1$-C$_4$)-alkyl, (C$_1$-C$_4$)-alkoxy, CF$_3$;
m$_D$ is 1 or 2;
v$_D$ is 0, 1, 2 or 3;
or of the formula (S4b) below, which are known, for example, from WO-A-99/16744,

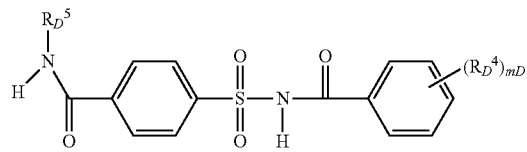
(S4b)

for example those in which
R$_D^5$=cyclopropyl and (R$_D^4$)=2-OMe ("cyprosulfamide", S4-1),
R$_D^5$=cyclopropyl and (R$_D^4$)=5-Cl-2-OMe (S4-2),
R$_D^5$=ethyl and (R$_D^4$)=2-OMe (S4-3),
R$_D^5$=isopropyl and (R$_D^4$)=5-Cl-2-OMe (S4-4) and
R$_D^5$=isopropyl and (R$_D^4$)=2-OMe (S4-5);
or of the formula (S4c), which are known, for example, from EP-A-365484,

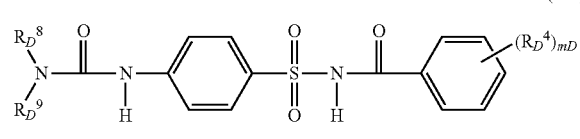
(S4c)

in which
R$_D^8$ and R$_D^9$ are each independently hydrogen, (C$_1$-C$_8$)-alkyl, (C$_3$-C$_8$)-cycloalkyl, (C$_3$-C$_6$)-alkenyl, (C$_3$-C$_6$)-alkynyl,
R$_D^4$ is halogen, (C$_1$-C$_4$)-alkyl, (C$_1$-C$_4$)-alkoxy, CF$_3$,
m$_D$ is 1 or 2;
for example
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea.
S5) Active ingredients from the class of the hydroxyaromatics and the aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 2,4-dichlorocinnamic acid, as described in WO-A-2004/084631, WO-A-2005/015994, WO-A-2005/016001.
S6) Active ingredients from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.
S7) Compounds of the formula (S7), as described in WO-A-1998/38856,

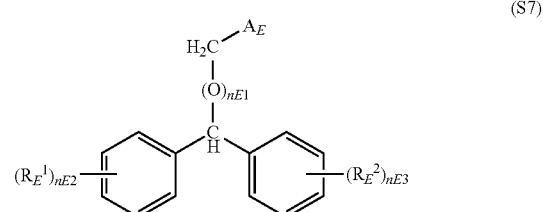
(S7)

where the symbols and indices are each defined as follows:
R$_E^1$, R$_E^2$ are each independently halogen, (C$_1$-C$_4$)alkyl, (C$_1$-C$_4$)alkoxy, (C$_1$-C$_4$)haloalkyl, (C$_1$-C$_4$)alkylamino, di-(C$_1$-C$_4$)alkylamino, nitro;
A$_E$ is COOR$_E^3$ or COSR$_E^4$
R$_E^3$, R$_E^4$ are each independently hydrogen, (C$_1$-C$_4$)alkyl, (C$_2$-C$_6$)alkenyl, (C$_2$-C$_4$)alkynyl, cyanoalkyl, (C$_1$-C$_4$)haloalkyl, phenyl, nitrophenyl, benzyl, halobenzyl, pyridinylalkyl and alkylammonium,
n$_E^1$ is 0 or 1;
n$_E^2$, n$_E^3$ are each independently 0, 1 or 2,
preferably diphenylmethoxyacetic acid, ethyl diphenylmethoxyacetate, methyl diphenylmethoxyacetate (CAS reg. no. 41858-19-9) (S7-1).
S8) Compounds of the formula (S8), as described in WO-A-98/27049,

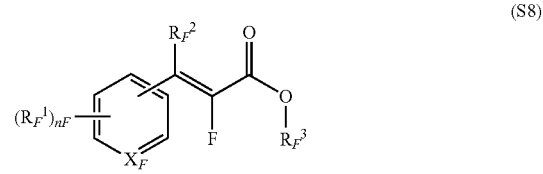
(S8)

in which
X$_F$ is CH or N,
if X$_F$=N is an integer from 0 to 4 and
if X$_F$=CH is an integer from 0 to 5,
R$_F^1$ is halogen, (C$_1$-C$_4$)-alkyl, (C$_1$-C$_4$)-haloalkyl, (C$_1$-C$_4$)-alkoxy, (C$_1$-C$_4$)-haloalkoxy, nitro, (C$_1$-C$_4$)-alkylthio, (C$_1$-C$_4$)-alkylsulfonyl, (C$_1$-C$_4$)-alkoxycarbonyl, optionally substituted phenyl, optionally substituted phenoxy,
R$_F^2$ is hydrogen or (C$_1$-C$_4$)-alkyl,
R$_F^3$ is hydrogen, (C$_1$-C$_8$)-alkyl, (C$_2$-C$_4$)-alkenyl, (C$_2$-C$_4$)-alkynyl or aryl, where each of the carbon-containing radicals mentioned above is unsubstituted or substituted by one or more, preferably by up to three, identical or different radicals from the group consisting of halogen and alkoxy; or salts thereof, preferably compounds in which $X_F$ is CH, $n_F$ is an integer from 0 to 2, $R_F^1$ is halogen, $(C_1$-$C_4)$-alkyl, $(C_1$-$C_4)$-haloalkyl, $(C_1$-$C_4)$-alkoxy, $(C_1$-$C_4)$-haloalkoxy, $R_F^2$ is hydrogen or $(C_1$-$C_4)$-alkyl, $R_F^3$ is hydrogen, $(C_1$-$C_8)$-alkyl, $(C_2$-$C_4)$-alkenyl, $(C_2$-$C_4)$-alkynyl or aryl, where each of the aforementioned carbon-containing radicals is unsubstituted or substituted by one or more, preferably by up to three, identical or different radicals from the group consisting of halogen and alkoxy; or salts thereof.

S9) Active ingredients from the class of the 3-(5-tetrazolylcarbonyl)-2-quinolones (S9), for example 1,2-dihydro-4-hydroxy-1-ethyl-3-(5-tetrazolylcarbonyl)-2-quinolone (CAS reg. no.: 219479-18-2), 1,2-dihydro-4-hydroxy-1-methyl-3-(5-tetrazolylcarbonyl)-2-quinolone (CAS reg. no.: 95855-00-8), as described in WO-A-1999/000020.

S10) Compounds of the formula (S10$^a$) or (S10$^b$) as described in WO-A-2007/023719 and WO-A-2007/023764

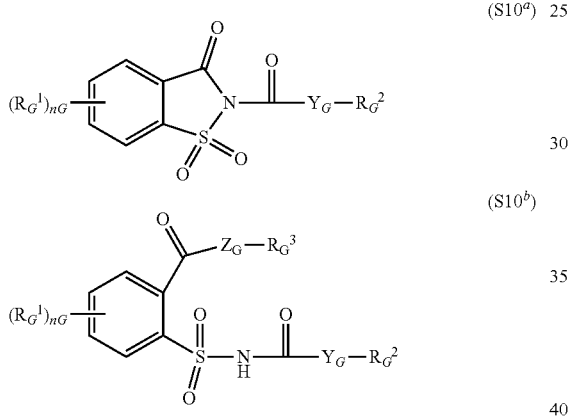

in which $R_G^1$ is halogen, $(C_1$-$C_4)$-alkyl, methoxy, nitro, cyano, $CF_3$, $OCF_3$ $Y_G$, $Z_G$ are each independently O or S, $n_G$ is an integer from 0 to 4, $R_G^2$ is $(C_1$-$C_{16})$-alkyl, $(C_2$-$C_6)$-alkenyl, $(C_3$-$C_6)$-cycloalkyl, aryl; benzyl, halobenzyl, $R_G^3$ is hydrogen or $(C_1$-$C_6)$-alkyl.

S11) Active ingredients of the oxyimino compound type (S11), which are known as seed-dressing compositions, for example "oxabetrinil" ((Z)-1,3-dioxolan-2-ylmethoxyimino(phenyl)acetonitrile) (S11-1), which is known as a seed-dressing safener for millet against damage by metolachlor, "fluxofenim" (1-(4-chlorophenyl)-2,2,2-trifluoro-1-ethanone O-(1,3-dioxolan-2-ylmethyl)oxime) (S11-2), which is known as a seed-dressing safener for millet against damage by metolachlor, and "cyometrinil" or "CGA-43089" ((Z)-cyanomethoxy-imino(phenyl)acetonitrile) (S11-3), which is known as a seed-dressing safener for millet against damage by metolachlor.

S12) Active ingredients from the class of the isothiochromanones (S12), for example methyl [(3-oxo-1H-2-benzothiopyran-4(3H)-ylidene)methoxy]acetate (CAS reg. no.: 205121-04-6) (S12-1) and related compounds from WO-A-1998/13361.

S13) One or more compounds from group (S13): "naphthalic anhydride" (1,8-naphthalenedicarboxylic anhydride) (S13-1), which is known as a seed-dressing safener for corn against damage by thiocarbamate herbicides, "fenclorim" (4,6-dichloro-2-phenylpyrimidine) (S13-2), which is known as a safener for pretilachlor in sown rice, "flurazole" (benzyl 2-chloro-4-trifluoromethyl-1,3-thiazole-5-carboxylate) (S13-3), which is known as a seed-dressing safener for millet against damage by alachlor and metolachlor, "CL 304415" (CAS reg. no. 31541-57-8) (4-carboxy-3,4-dihydro-2H-1-benzopyran-4-acetic acid) (S13-4) from American Cyanamid, which is known as a safener for corn against damage by imidazolinones, "MG 191" (CAS reg. no. 96420-72-3) (2-dichloromethyl-2-methyl-1,3-dioxolane) (S13-5) from Nitrokemia, which is known as a safener for corn, "MG-838" (CAS reg. no. 133993-74-5) (2-propenyl 1-oxa-4-azaspiro[4.5]decane-4-carbodithioate) (S13-6) from Nitrokemia, "disulfoton" (O,O-diethyl S-2-ethylthioethyl phosphorodithioate) (S13-7), "dietholate" (O,O-diethyl O-phenylphosphorothioate) (S13-8), "mephenate" (4-chlorophenyl methyl carbamate) (S13-9).

S14) Active ingredients which, in addition to herbicidal action against harmful plants, also have safener action on crop plants such as rice, for example "dimepiperate" or "MY-93" (S-1-methyl-1-phenylethylpiperidine-1-carbothioate), which is known as a safener for rice against damage by the herbicide molinate, "daimuron" or "SK 23" (1-(1-methyl-1-phenylethyl)-3-p-tolylurea), which is known as a safener for rice against damage by the herbicide imazosulfuron, "cumyluron" ="JC-940" (3-(2-chlorophenylmethyl)-1-(1-methyl-1-phenylethyl)urea, see JP-A-60087254), which is known as a safener for rice against damage by some herbicides, "methoxyphenon" or "NK 049" (3,3'-dimethyl-4-methoxybenzophenone), which is known as a safener for rice against damage by some herbicides, "CSB" (1-bromo-4-(chloromethylsulfonyl)benzene) from Kumiai, (CAS reg. no. 54091-06-4), which is known as a safener against damage by some herbicides in rice.

S15) Compounds of the formula (S15) or tautomers thereof as described in WO-A-2008/131861 and WO-A-2008/131860

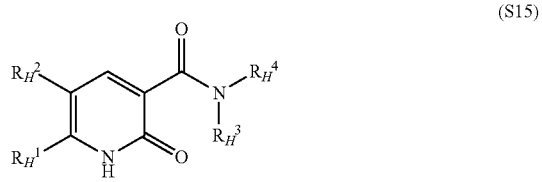

in which $R_H^1$ is a $(C_1$-$C_6)$haloalkyl radical and $R_H^2$ is hydrogen or halogen and $R_H^3$, $R_H^4$ are each independently hydrogen, $(C_1$-$C_{16})$alkyl, $(C_2$-$C_{16})$alkenyl or $(C_2$-$C_{16})$alkynyl, where each of the 3 latter radicals is unsubstituted or substituted by one or more radicals from the group of halogen, hydroxyl, cyano, $(C_1$-$C_4)$alkoxy, $(C_1$-$C_4)$haloalkoxy, $(C_1$-$C_4)$alkylthio, $(C_1$-$C_4)$alkylamino, di[$(C_1$-$C_4)$alkyl]amino, [$(C_1$-$C_4)$alkoxy]carbonyl, [$(C_1$-$C_4)$haloalkoxy]carbonyl, $(C_3$-$C_6)$cycloalkyl which is unsubstituted or substituted, phenyl which is unsubstituted or substituted, and heterocyclyl which is unsubstituted or substituted, or $(C_3$-$C_6)$ cycloalkyl, (C₄-C₆)cycloalkenyl, (C₃-C₆)cycloalkyl which is fused on one side of the ring to a 4- to 6-membered saturated or unsaturated carbocyclic ring, or (C₄-C₆)cycloalkenyl which is fused on one side of the ring to a 4- to 6-membered saturated or unsaturated carbocyclic ring, where each of the 4 latter radicals is unsubstituted or substituted by one or more radicals from the group of halogen, hydroxyl, cyano, (C₁-C₄)alkyl, (C₁-C₄)haloalkyl, (C₁-C₄)alkoxy, (C₁-C₄)haloalkoxy, (C₁-C₄)alkylthio, (C₁-C₄)alkylamino, di[(C₁-C₄)alkyl] amino, [(C₁-C₄)alkoxy]carbonyl, [(C₁-C₄)haloalkoxy] carbonyl, (C₃-C₆)cycloalkyl which is unsubstituted or substituted, phenyl which is unsubstituted or substituted, and heterocyclyl which is unsubstituted or substituted, or $R_H^3$ is (C₁-C₄)-alkoxy, (C₂-C₄)alkenyloxy, (C₂-C₆)alkynyloxy or (C₂-C₄)haloalkoxy and $R_H^4$ is hydrogen or (C₁-C₄)-alkyl or $R_H^3$ and $R_H^4$ together with the directly bonded nitrogen atom are a four- to eight-membered heterocyclic ring which, in addition to the nitrogen atom, may also contain further ring heteroatoms, preferably up to two further ring heteroatoms from the group of N, O and S, and which is unsubstituted or substituted by one or more radicals from the group of halogen, cyano, nitro, (C₁-C₄)alkyl, (C₁-C₄) haloalkyl, (C₁-C₄)alkoxy, (C₁-C₄)haloalkoxy and (C₁-C₄) alkylthio.

S16) Active ingredients which are used primarily as herbicides but also have safener action on crop plants, for example (2,4-dichlorophenoxy)acetic acid (2,4-D), (4-chlorophenoxy)acetic acid, (R,S)-2-(4-chloro-o-tolyloxy)propionic acid (mecoprop), 4-(2,4-dichlorophenoxy) butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyl)ethyl 3,6-dichloro-2-methoxybenzoate (lactidichlor-ethyl).

Substances which influence plant maturity:

Usable combination partners for the compounds according to formula (I) when used according to present invention in mixture formulations or in a tankmix are, for example, known active ingredients based on inhibition of, for example, 1-aminocyclopropane-1-carboxylate synthase, 1-aminocyclopropane-1-carboxylate oxidase and the ethylene receptors, e.g. ETR1, ETR2, ERS1, ERS2 or EIN4, as described, for example, in Biotechn. Adv. 2006, 24, 357-367; Bot. Bull. Acad. Sin. 199, 40, 1-7 or Plant Growth Reg. 1993, 13, 41-46 and literature cited therein.

Examples of known substances which influence plant maturity and can be combined with the inventive compounds include the active ingredients which follow (the compounds are designated by the "common name" according to the International Organization for Standardization (ISO) or by the chemical name or by the code number) and always encompass all use forms, such as acids, salts, esters and isomers, such as stereoisomers and optical isomers. By way of example, one use form and in some cases a plurality of use forms are mentioned:

rhizobitoxine, 2-aminoethoxyvinylglycine (AVG), methoxyvinylglycine (MVG), vinylglycine, aminooxyacetic acid, sinefungin, S-adenosylhomocysteine, 2-keto-4-methyl thiobutyrate, 2-(methoxy)-2-oxoethyl (isopropylidene)aminooxyacetate, 2-(hexyloxy)-2-oxoethyl (isopropylidene)aminooxyacetate, 2-(isopropyloxy)-2-oxoethyl (cyclohexylidene)aminooxyacetate, putrescine, spermidine, spermine, 1,8-diamino-4-aminoethyloctane, L-canaline, daminozide, methyl 1-aminocyclopropyl-1-carboxylate, N-methyl-1-aminocyclopropyl-1-carboxylic acid, 1-aminocyclopropyl-1-carboxamide, substituted 1-aminocyclopropyl-1-carboxylic acid derivatives as described in DE3335514, EP30287, DE2906507 or U.S. Pat. No. 5,123,951, 1-aminocyclopropyl-1-hydroxamic acid, 1-methylcyclopropene, 3-methylcyclopropene, 1-ethylcyclopropene, 1-n-propylcyclopropene, 1-cyclopropenylmethanol, carvone, eugenol, sodium cycloprop-1-en-1-ylacetate, sodium cycloprop-2-en-1-ylacetate, sodium 3-(cycloprop-2-en-1-yl)propanoate, sodium 3-(cycloprop-1-en-1-yl)propanoate, jasmonic acid, methyl jasmonate, ethyl jasmonate.

Substances which influence plant health and germination:

Usable combination partners for the inventive compounds in mixture formulations or in a tankmix are, for example, known active ingredients that influence plant health or germination. Examples of known substances influencing plant health and germination and can be combined with the inventive compounds include the active ingredients which follow (the compounds are designated by the "common name" according to the International Organization for Standardization (ISO) or by the chemical name or by the code number) and always encompass all use forms, such as acids, salts, esters and isomers, such as stereoisomers and optical isomers. By way of example, one use form and in some cases a plurality of use forms are mentioned): sarcosine, phenyl alanine, tryptophan, N'-methyl-1-phenyl-1-N,N-diethylaminomethanesulfonamide, Apio-galacturonane as described in WO2010017956, 4-oxo-4-[(2-phenylethyl) amino]butanoic acid, 4-{[2-(1 H-indole-3-yl)ethyl]amino}-4-oxobutanoic acid, 4-[(3-methylpyridin-2-yl)amino]-4-oxobutanoic acid, allantoine, 5-amino levulinic acid, (2S, 3R)-2-(3,4-dihydroxyphenyl)-3,4-dihydro-2H-chromene-3, 5,7-triol and structurally related catechines as described in WO2010122956, 2-Hydroxy-4-(methylsulfanyl)butanoic acid, (3E,3αR,8βS)-3-({[(2R)-4-methyl-5-oxo-2,5-dihydrofuran-2-yl]oxy}methylene)-3,3α,4,8β-tetrahydro-2H-indeno[1,2-b]furan-2-one and related lactons as described in EP2248421, abscisic acid, (2Z,4E)-5-[6-Ethynyl-1-hydroxy-2,6-dimethyl-4-oxocyclohex-2-en-1-yl]-3-methylpenta-2,4-dienoic acid, Methyl-(2Z,4E)-5-[6-ethinyl-1-hydroxy-2,6-dimethyl-4-oxocyclohex-2-en-1-yl]-3-methylpenta-2,4-dienoate Herbicides or plant growth regulators:

Usable combination partners for the inventive use of compounds of formula (I) in mixture formulations or in a tankmix are, for example, known active ingredients based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoendesaturase, photosystem I, photosystem II, protoporphyrinogen oxidase, gibberellin biosynthesis, as described, for example, in Weed Research 26 (1986) 441-445 or "The Pesticide Manual", 15th edition, The British Crop Protection Council and the Royal Soc. of Chemistry, 2009 and literature cited therein.

Examples of known herbicides or plant growth regulators which can be combined with the inventive compounds include the active ingredients which follow (the compounds are designated by the "common name" according to the International Organization for Standardization (ISO) or by the chemical name or by the code number) and always encompass all use forms, such as acids, salts, esters and isomers, such as stereoisomers and optical isomers. By way of example, one use form and in some cases a plurality of use forms are mentioned:

Possible mixing partners from the group of herbicides are: acetochlor, aciﬂuorfen, aciﬂuorfen-sodium, aclonifen, alachlor, allidochlor, alloxydim, alloxydim-sodium, ametryn, amicarbazone, amidochlor, amidosulfuron, aminocyclopyrachlor, aminocyclopyrachlor-potassium, aminocyclopyrachlor-methyl, aminopyralid, amitrole, ammoniumsulfamate, anilofos, asulam, atrazine, azafenidin, azimsulfuron, beﬂubutamid, benazolin, benazolin-ethyl, benﬂuralin, benfuresate, bensulfuron, bensulfuron-methyl, bensulide, bentazone, benzobicyclon, benzofenap, bicyclopyrone, bifenox, bilanafos, bilanafos-sodium, bispyribac, bispyribac-sodium, bromacil, bromobutide, bromofenoxim, bromoxynil, bromoxynil-potassium, bromoxynil-heptanoate, bromoxynil-octanoate, bromoxynil-butyrate, busoxinone, butachlor, butafenacil, butamifos, butenachlor, butralin, butroxydim, butylate, cafenstrole, carbetamide, carfentrazone, carfentrazone-ethyl, chloramben, chlorbromuron, chlorfenac, chlorfenac-sodium, chlorfenprop, chlorﬂurenol, chlorﬂurenol-methyl, chloridazon, chlorimuron, chlorimuron-ethyl, chlorophthalim, chlorotoluron, chlorthal-dimethyl, chlorsulfuron, cinidon, cinidon-ethyl, cinmethylin, cinosulfuron, clethodim, clodinafop, clodinafop-propargyl, clomazone, clomeprop, clopyralid, cloransulam, cloransulam-methyl, cumyluron, cyanamide, cyanazine, cycloate, cyclosulfamuron, cycloxydim, cyhalofop, cyhalofop-butyl, cyprazine, 2,4-D, 2,4-D-butotyl, -butyl, -dimethylammonium, -diolamin, -ethyl, -2-ethylhexyl, -isobutyl, -isooctyl, -isopropylammonium, -potassium, -triisopropanolammon ium and -trolamine, 2,4-DB, 2,4-DB-butyl, -dimethylammonium, -isooctyl, -potassium and -sodium, daimuron (dymron), dalapon, dazomet, n-decanol, desmedipham, detosyl-pyrazolate (DTP), dicamba, dichlobenil, dichlorprop, dichlorprop-P, diclofop, diclofop-methyl, diclofop-P-methyl, diclosulam, difenzoquat, diﬂufenican, diﬂufenzopyr, diﬂufenzopyr-sodium, dimefuron, dimepiperate, dimethachlor, dimethametryn, dimethenamid, dimethenamid-P, dimetrasulfuron, dinitramine, dinoterb, diphenamid, diquat, diquat-dibromid, dithiopyr, diuron, DNOC, endothal, EPTC, esprocarb, ethalﬂuralin, ethametsulfuron, ethametsulfuron-methyl, ethiozin, ethofumesate, ethoxyfen, ethoxyfen-ethyl, ethoxysulfuron, etobenzanid, F-5331, i.e. N-[2-chloro-4-ﬂuoro-5-[4-(3-ﬂuoropropyl)-4,5-dihydro-5-oxo-1H-tetrazol-1-yl]-phenyl]-ethansulfonamide, F-7967, i.e. 3-[7-chloro-5-ﬂuor-2-(triﬂuoromethyl)-1H-benzimidazol-4-yl]-1-methyl-6-(triﬂuormethyl)pyrimidin-2,4(1H, 3H)-dion, fenoxaprop, fenoxaprop-P, fenoxaprop-ethyl, fenoxaprop-P-ethyl, fenoxasulfone, fentrazamide, ﬂamprop, ﬂamprop-M-isopropyl, ﬂamprop-M-methyl, ﬂazasulfuron, ﬂorasulam, ﬂuazifop, ﬂuazifop-P, ﬂuazifop-butyl, ﬂuazifop-P-butyl, ﬂucarbazone, ﬂucarbazone-sodium, ﬂucetosulfuron, ﬂuchloralin, ﬂufenacet (thiaﬂuamide, ﬂuthiamide), ﬂufenpyr, ﬂufenpyr-ethyl, ﬂumetsulam, ﬂumiclorac, ﬂumiclorac-pentyl, ﬂumioxazin, ﬂuometuron, ﬂuoroglycofen, ﬂuoroglycofen-ethyl, ﬂupropanate, ﬂupyrsulfuron, ﬂupyrsulfuron-methyl-sodium, ﬂurenol, ﬂurenol-butyl, ﬂuridone, ﬂurochloridone, ﬂuroxypyr, ﬂuroxypyr-meptyl, ﬂurtamone, ﬂuthiacet, ﬂuthiacet-methyl, ﬂuthiamide, fomesafen, fomesafen-sodium, foramsulfuron, fosamine, glufosinate, glufosinate-ammonium, glufosinate-P, glufosinate-P-ammonium, glufosinate-P-sodium, glyphosate, glyphosate-isopropylammonium, -ammonium, -diammonium, -dimethylammonium, -potassium, -sodium and -trimesium, H-9201, i.e. O-(2,4-Dimethyl-6-nitrophenyl)-O-ethyl-isopropylphosphoramidothioat, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)-ethyl-(2,4-dichlorphenoxy)acetate, imazamethabenz, lmazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-ammonium, imazosulfuron, indanofan, indaziﬂam, iodosulfuron, iodosulfuron-methyl-sodium, ioxynil, ioxynil-sodium, ioxynil-potassium, ioxynil-octanoate, ipfencarbazone, isoproturon, isouron, isoxaben, isoxaﬂutole, karbutilate, KUH-043, i.e. 3-({[5-(diﬂuoromethyl)-1-methyl-3-(triﬂuormethyl)-1H-pyrazol-4-yl]methyl}sulfonyl)-5,5-dimethyl-4,5-dihydro-1,2-oxazole, ketospiradox, lactofen, lenacil, linuron, MCPA (salts and esters), MCPB (salts and esters), MCPB-methyl, -ethyl and -sodium, mecoprop, mecoprop-sodium, and -butotyl, mecoprop-P, mecoprop-P-butotyl, -dimethylammonium, -2-ethylhexyl and -potassium, mefenacet, meﬂuidide, mesosulfuron, mesosulfuron-methyl, mesotrione, metam, metamifop, metamitron, metazachlor, metazosulfuron, methabenzthiazuron, methiopyrisulfuron, methiozolin, methyl isothiocyanate, metobromuron, metolachlor, S-metolachlor, metosulam, metoxuron, metribuzin, metsulfuron, metsulfuron-methyl, molinate, monolinuron, monosulfuron, monosulfuron-ester, MT-128, i.e. 6-chloro-N-[(2E)-3-chlorprop-2-en-1-yl]-5-methyl-N-phenylpyridazin-3-amine, MT-5950, i.e. N-[3-chloro-4-(1-methylethyl)-phenyl]-2-methylpentanamide, NGGC-011, napropamide, NC-310, i.e. 4-(2,4-Dichlorbenzoyl)-1-methyl-5-benzyloxypyrazol, neburon, nicosulfuron, nonanoic acid, norﬂurazon, oleic acid (fatty acids), orbencarb, orthosulfamuron, oryzalin, oxadiargyl, oxadiazon, oxasulfuron, oxaziclomefon, oxyﬂuorfen, paraquat, paraquat dichloride, pebulate, pelargonic acid (Nonansäure), pendimethalin, penoxsulam, pentachlorphenol, pentoxazone, pethoxamid, petroleum oils, phenmedipham, phenmedipham-ethyl, picloram, picolinafen, pinoxaden, piperophos, pretilachlor, primisulfuron, primisulfuron-methyl, prodiamine, priﬂuraline, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraﬂufen, pyraﬂufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saﬂufenacil, sethoxydim, siduron, simazine, simetryn, sulcotrione, sulfentrazone, sulfometuron, sulfometuron-methyl, sulfosate, sulfosulfuron, SW-065, SYN-523, SYP-249, i.e. 1-ethoxy-3-methyl-1-oxobut-3-en-2-yl-5-[2-chlor-4-(triﬂuormethyl)phenoxy]-2-nitrobenzoate, SYP-300, i.e. 1-[7-ﬂuoro-3-oxo-4-(prop-2-in-1-yl)-3,4-dihydro-2H-1,4-benzoxazin-6-yl]-3-propyl-2-thioxoimidazolidin-4,5-dione, TCA (trichloroacetic acid), TCA-sodium, tebuthiuron, tefuryltrione, tembotrione, tepraloxydim, terbacil, terbucarb, terbumeton, terbuthylazin, terbutryn, thenylchlor, thiazopyr, thiencarbazone, thiencarbazone-methyl, thifensulfuron, thifensulfuron-methyl, thiobencarb, topramezone, tralkoxydim, triafamone, triallate, triasulfuron, triaziﬂam, tribenuron, tribenuron-methyl, triclopyr, trietazine, triﬂoxysulfuron, triﬂoxysulfuron-sodium, triﬂuralin, triﬂusulfuron, triﬂusulfuron-methyl, tritosulfuron, urea sulfate, vernolate, ZJ-0862, i.e. 3,4-dichloro-N-{2-[(4,6-dimethoxypyrimidin-2-yl)oxy]benzyl}aniline, as well as the following compounds:

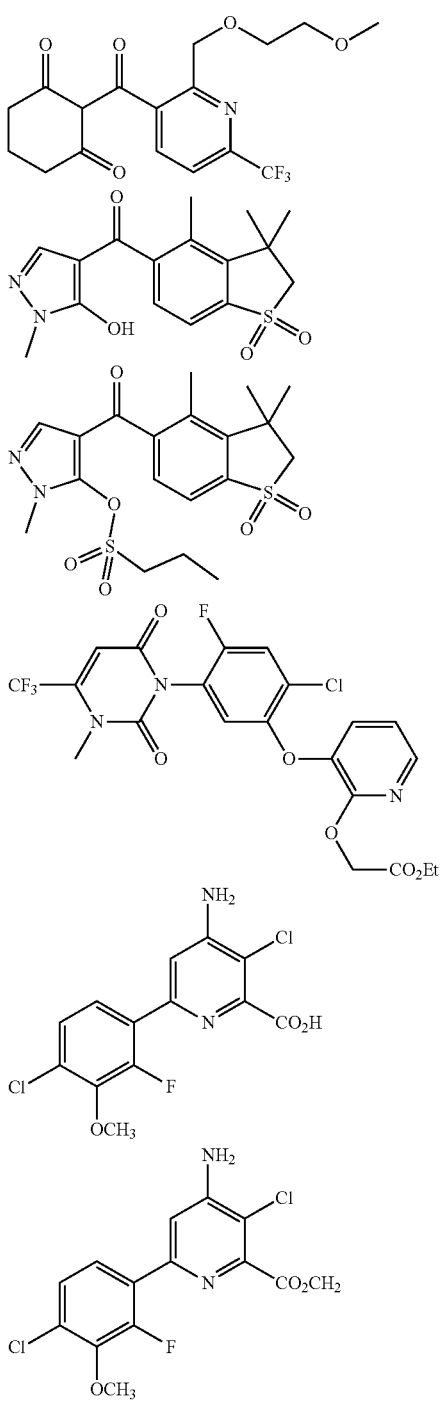

Possible mixing partners from the group of plant-growth regulators are, for example: abscisic acid, acibenzolar, acibenzolar-S-methyl, 5-aminolaevulinic acid, ancymidol, 6-benzylaminopurine, brassinolide, catechin, cloprop, cyclanilide, 3-(cycloprop-1-enyl)propionic acid, 3-(cycloprop-1-enyl)propionic acid, sodium salt, daminozide, dazomet, n-decanol, dikegulac, dikegulac-sodium, endothal, flumetralin, flurenol, flurenol-butyl, flurprimidol, forchlorfenuron, gibberellic acid, inabenfide, indol-3-acetic acid (IAA), 4-indol-3-ylbutyric acid, isoprothiolane, jasmonic acid, methyl jasmonate, kinetin, maleic hydrazide, mepiquat chloride, 1-methylcyclopropene, 2-(1-naphthyl)acetamide, 1-naphthylacetic acid, 2-naphthyloxyacetic acid, nitrophenolate-mixture, 4-oxo-4[(2-phenylethyl)amino]butanoic acid, paclobutrazol, N-phenylphthalamic acid, probenazol, prohexadione, prohexadione-calcium, prohydrojasmone, propham, salicylic acid, Strigolacton, tecnazene, thidiazuron, triacontanol, trinexapac, tsitodef, uniconazole, uniconazole-P.

The invention is to be illustrated by the biological examples which follow, but without restricting it thereto.

BIOLOGICAL EXAMPLES

A) Testing Conditions
A1) Testing Conditions in Glasshouse Trials
The trials can be carried out in a glasshouse under normal good growth conditions for the plants using pot trials with 8 cm diameter pots. Each pot contains 6-8 plants. The results are the average of two replicates.

The applications can be done with seed treatment, pre-emergence or post-emergence treatments. The pre- or post-emergence applications cam be made with spray applications using 100-300 l/water per hectare.

The assessments shall be done via visual ratings (0-100% scale, several days after the application, comparing treated vs. untreated checks pots).

A2) Testing Conditions in a Growth Chamber
Into each 16 cm diameter pot containing 3 liters loamy soil, one Triticum aestivum (TRZAS), variety "AC harvest" kernel was sawn. Obtained results were the average of five replicates.

The plants were grown in a growth chamber under slightly reduced water conditions but otherwise normal and good growing conditions.

Spray application—with spray applications using 100-300 l/water per hectare—was done at a plant growth stage of 56-61, according to the BBCH scheme.

The trials have been harvested after crops reached the full maturity. After the harvest, the total weights of grains (kernels/seeds) per pot were taken.

The results are dicslosed under C1, below.

A3) Testing Conditions in Field Trials
The trials can be carried out under natural field conditions (plot trials, 10 square meter plots, 2-4 replications).

The applications can be done with seed treatment, pre- or post-emergence treatments straight (alone, 1 application) or sequential treatments e.g. seed treatment followed by pre-emergence and/or post-emergence spray applications. The pre- or post-emergence applications can be made with spray applications using 100-300 l/water per hectare. The growth stage of the crops species at the time of application are reported in the result tables.

The assessments shall be done via visual ratings (0-100% scale) or counting. The trials will be harvested after crops reached the full maturity. After the harvest the total weight of kernels/seeds/beets per plot will be measured. The results are reported as means over 2-4 replications.

A4) Seed Treatment Conditions
The active ingredients can be applied to the untreated, dry seeds together with a carrier. After a short period of time to let the seeds dry, they will be ready to be sown in the pot or field using standard equipments.

The results are dicslosed under C2, below.

B) Abbreviations in the Result Tables
Dose rate g/ai=dose rates in gram active ingredient per hectare
ai=active ingredient (based on 100% content)

Compound (A1)=N-(2-methoxybenzoyl)-4-[(methylaminocarbonyl)amino]benzenesulfonamide UTC=untreated control plots post-emergence=applied(sprayed) after emergence of the crop plants (the growth stage of the plants at the time of application is reported in the tables accordingly)

yield=harvested weight of mature grains(seeds/kernels) pro hectare (ha); adjusted to 86% dry weight resp. 14% moisture C1) Results Obtained from Growth Chamber Trials

TABLE C1-1

Grain yield of *Triticum aestivum* variety "AC Harvest" after treatement with Compound (A1), several fungicides and insecticides and mixtures of Compound (A1) = N-(2-methoxybenzoyl)-4-[(methylaminocarbonyl)amino]-benzenesulfonamide and the resepective fungicides and insecticides

| Active ingredient (s) | Dose rate gai/ha [1] | Grain Yield, g/plant | Relative, % | Difference (%) vs. UTC |
|---|---|---|---|---|
| UTC | — | 1.06 | 100.0 | — |
| Compound (A1) = A1 | 10 | 1.19 | 112.3 | +12.3 |
| Clothianidin (I-3) | 10 | 1.19 | 112.3 | +12.3 |
| A1 + clothianidin | 10 + 10 | 1.31 | 123.6 | +23.6 |
| Thiamethoxam (I-19) | 10 | 1.30 | 122.6 | +22.6 |
| A1 + Thiamethoxam | 10 + 10 | 1.39 | 131.1 | +32.1 |
| Fipronil (I-8) | 10 | 1.19 | 112.3 | +12.3 |
| A1 + fipronil | 10 + 10 | 1.38 | 120.2 | +20.2 |
| Imidacloprid (I-11) | 10 | 1.14 | 107.5 | +7.5 |
| A1 + imidacloprid | 10 + 10 | 1.37 | 129.2 | +29.2 |
| Pyraclostrobin (F-57) | 10 | 1.24 | 117.0 | +17.0 |
| A1 + pyraclostrobin | 10 + 10 | 1.35 | 127.4 | +27.4 |
| Azoxystrobin (F-47) | 10 | 1.22 | 115.1 | +15.1 |
| A1 + azoxystrobin | 10 + 10 | 1.33 | 125.5 | +25.5 |
| Trifloxystrobin (F-60) | 10 | 1.12 | 105.7 | +5.7 |
| A1 + trifloxystrobin | 10 + 10 | 1.39 | 131.1 | +31.1 |
| Prothioconazole (F-124) | 10 | 1.02 | 96.2 | −3.8 |
| A1 + prothioconazole | 10 + 10 | 1.31 | 123.6 | +23.6 |
| Difenoconazole (F-105) | 10 | 1.02 | 96.2 | −3.8 |
| A1 + difenoconazole | 10 + 10 | 1.37 | 129.2 | +29.2 |

C2) Results Obtained from Seed Treatment

TABLE C2-1

*Triiticum aestivum* seeds (TRZAS) treated according to conditions disclosed under A4, above

| Active ingredient (s) | Dose rate gai/kg seed | Grain Yield, g/plant | Relative, % | Difference (%) vs. UTC |
|---|---|---|---|---|
| UTC | — | 1.80 | 100.0 | — |
| Compound (A1) = A1 | 0.5 | 1.90 | 105.6 | +5.6 |
| Compound (A1) = A1 | 1.0 | 1.87 | 103.9 | +3.9 |
| Metalaxyl (F-10) | 1 | 1.52 | 84.4 | −15.6 |
| A1 + Metalaxyl | 0.5 + 1 | 2.46 | 136.7 | +36.7 |
| A1 + Metalaxyl | 1 + 1 | 2.64 | 146.7 | +46.7 |
| Fludioxonil (F-83) | 1 | 2.06 | 114.4 | +14.4 |
| A1 + Fludioxonil | 1 + 1 | 2.51 | 139.4 | +39.4 |
| Difenoconazole (F-105) | 1 | 1.62 | 90 | −10 |
| A1 + difenoconazole | 0.5 + 1 | 2.64 | 146.7 | +46.7 |
| A1 + difenoconazole | 1 + 1 | 2.56 | 142.2 | +42.2 |

The invention claimed is:

1. A method for including specific growth regulating responses on useful plants and/or crop plants, seeds from which they grow, and/or on the locus in which they grow in their normal habitat, thereby increasing yield of the useful plants and/or crop plants with respect to harvested plant organs, said method comprising applying (a) N-(2-methoxybenzoyl)-4-[(methylaminocarbonyl)amino]benzenesulfonamide in combination with (b) one or more compounds selected from the group consisting of, trifloxystrobin, difenoconazole, metalaxyl, and fludioxonil in an effective, non-phytotoxic amount to crop and/or useful plants, seeds from which said plants grow, and/or to the locus in which said plants grow in a normal habitat, wherein the achieved yield with application of (a) and (b) together is greater than achieved by (a) or (b) alone.

2. The method according to claim 1, wherein said yield increase is an increase in the grain yield of crop plants selected from group consisting of cereals, canola, soybean and cotton crops.

3. The method according to claim 1, wherein said yield increase is an increase in the gluten content of seed kernels of crop plants selected from group consisting of cereals, canola and soybean crops.

4. The method according to claim 1, wherein said yield increase is an increase in the gluten content of seed kernels of crop plants selected from group consisting of cereal crops.

5. The method according to claim 1, wherein said yield increase is an increase in the protein content of seed kernels of crop plants selected from group consisting of cereals, canola and soybean crops.

6. The method according to claim 1, wherein said yield increase is an increase in the yield of the amount by weight of beets of beet plants.

7. The method according to claim 1, wherein said yield increase is an increase in the sugar content of sugar plants.

8. The method according to claim 1, wherein said yield increase is an increase in the biomass yield maize plants growing in the absence of extraordinary environmental conditions.

9. The method according to claim 1, wherein yield increase is an increase in the biomass yield of sugar plants.

10. The method according to claim 1, wherein the N-(2-methoxybenzoyl)-4-[(methylaminocarbonyl)amino]benzenesulfonamide in combination with one or more compounds selected from the group consisting of trifloxystrobin, difenoconazole, metalaxyl, and fludioxonil is applied to said plants, wherein the plants grow in a normal habitat in the absence of extraordinary environmental conditions.

11. The method according to claim 1, wherein the N-(2-methoxybenzoyl)-4-[(methylaminocarbonyl)amino]benzenesulfonamide in combination with one or more compounds selected from the group consisting of trifloxystrobin, difenoconazole, metalaxyl, and fludioxonil is applied to said plants in the absence of abiotic stress.

12. The method according to claim 1, wherein the N-(2-methoxybenzoyl)-4-[(methylaminocarbonyl)amino]benzenesulfonamide is applied to said plants at an application rate of 0.05 to 1000 g/ha in combination with one or more compounds selected from the group consisting of trifloxystrobin, difenoconazole, metalaxyl, and fludioxonil.

13. The method according to claim 1, wherein the N-(2-methoxybenzoyl)-4-[(methylaminocarbonoyl)amino]benzensulfonamide is applied to said plants at an application rate of 25 to 100 g/ha in combination with one or more compounds selected from the group consisting of trifloxystrobin, difenoconazole, metalaxyl, and fludioxonil.

14. The method according to claim 1, wherein N-(2-methoxybenzoyl)-4-[(methylaminocarbonyl)amino]benzenesulfonamide is applied in combination with trifloxystrobin.

15. The method according to claim 1, wherein the N-(2-methoxybenzoyl)-4-[(methylaminocarbonyl)amino]benzenesulfonamide is applied additionally in combination with prothioconazole.

16. A method for inducing specific growth regulating responses on useful plants and/or crop plants, seeds from which they grow and/or on the locus in which they grow in their normal habitat, thereby increasing yield of the useful plants and/or crop plants with respect to harvested plant organs, said method comprising applying (a)N-(2-methoxybenzoyl)-4-[(methylaminocarbonyl) amino]benzenesulfonamide in combination with (ii) trifloxystrobin and propiconazole or (vi) bixafen and trifloxystrobin, in an effective, non-phytotoxic amount to crop and/or useful plants grow in a normal habitat, wherein the achieved yield with application of (a) and (ii) or (vi) together due to the presence of trifoxystrobin in (ii) and (vi) is greater than achieved by (a) or (ii) or (vi) alone.

17. A method for inducing specific growth regulating responses on useful plants and/or crop plants, seeds from which they grow, and/or in the locus in which they grow in their normal habitat, thereby increasing yield of the useful plants and/or crop plants with respect to harvested plant organs, said method comprising said applying (a) N-(2-methoxybenzoyl)-4-[(methylaminocarbonyl)amino]benzenesulfonamide in combination with (b) one or more compounds selected from the group consisting of trifloxyxtrobin, difenoconazole, metalaxyl, and fludioxonil, and (c) one or more compounds selected from the group consisting of chlormequat-chloride, ethephon, mepiquat, trinexapac-ethyl, 2, 4-D, MCPA, and 2, 4-D Choline in an effective, non-phytotoxic amount to crop and/or useful plants, seeds from which said plants grow, and/or to the locus in which said plants grow in a normal habitat, wherein the achieved yield with application of (a) and (b) together is greater than achieved by (a) or (b) alone.

\* \* \* \* \*